United States Patent
Heil et al.

(10) Patent No.: US 11,063,221 B2
(45) Date of Patent: *Jul. 13, 2021

(54) MATERIALS FOR ELECTRONIC DEVICES

(71) Applicant: Merck Patent GmbH, Darmstadt (DE)

(72) Inventors: Holger Heil, Frankfurt am Main (DE); Lara-Isabel Rodriguez, Darmstadt (DE); Beate Burkhart, Darmstadt (DE); Sebastian Meyer, Acchaffenburg (DE)

(73) Assignee: Merck Patent GmbH, Darmstadt (DE)

( * ) Notice: Subject to any disclaimer, the term of this patent is extended or adjusted under 35 U.S.C. 154(b) by 177 days.

This patent is subject to a terminal disclaimer.

(21) Appl. No.: 15/304,118

(22) PCT Filed: Mar. 17, 2015

(86) PCT No.: PCT/EP2015/000587
§ 371 (c)(1),
(2) Date: Oct. 14, 2016

(87) PCT Pub. No.: WO2015/158409
PCT Pub. Date: Oct. 22, 2015

(65) Prior Publication Data
US 2017/0125686 A1    May 4, 2017

(30) Foreign Application Priority Data
Apr. 16, 2014 (EP) .................. 14001391

(51) Int. Cl.
| | | |
|---|---|---|
| *H01L 51/00* | (2006.01) | |
| *C07C 15/38* | (2006.01) | |
| *C07D 235/18* | (2006.01) | |
| *C07C 255/50* | (2006.01) | |
| *C07C 13/62* | (2006.01) | |
| *C07D 213/16* | (2006.01) | |
| *C07C 13/28* | (2006.01) | |
| *C07C 13/465* | (2006.01) | |
| *C07D 251/24* | (2006.01) | |
| *C07D 239/26* | (2006.01) | |
| *C09B 57/00* | (2006.01) | |
| *C09B 1/00* | (2006.01) | |
| *C07C 1/30* | (2006.01) | |
| *C07C 253/30* | (2006.01) | |
| *C07C 255/52* | (2006.01) | |
| *H01L 51/50* | (2006.01) | |
| *C09K 11/02* | (2006.01) | |
| *H01L 51/42* | (2006.01) | |
| *H01L 51/05* | (2006.01) | |

(52) U.S. Cl.
CPC .......... *H01L 51/0058* (2013.01); *C07C 1/30* (2013.01); *C07C 13/28* (2013.01); *C07C 13/465* (2013.01); *C07C 13/62* (2013.01); *C07C 15/38* (2013.01); *C07C 253/30* (2013.01); *C07C 255/50* (2013.01); *C07C 255/52* (2013.01); *C07D 213/16* (2013.01); *C07D 235/18* (2013.01); *C07D 239/26* (2013.01); *C07D 251/24* (2013.01); *C09B 1/00* (2013.01); *C09B 57/00* (2013.01); *C09B 57/001* (2013.01); *C09K 11/025* (2013.01); *H01L 51/0054* (2013.01); *C07C 2601/02* (2017.05); *C07C 2601/14* (2017.05); *C07C 2602/08* (2017.05); *C07C 2603/24* (2017.05); *C07C 2603/26* (2017.05); *C07C 2603/42* (2017.05); *C07C 2603/50* (2017.05); *C07C 2603/52* (2017.05); *H01L 51/006* (2013.01); *H01L 51/0545* (2013.01); *H01L 51/42* (2013.01); *H01L 51/50* (2013.01); *H01L 51/5012* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| | | | | |
|---|---|---|---|---|
| 7,829,206 | B2 * | 11/2010 | Kubota ................ | C07C 13/567 428/690 |
| 8,986,852 | B2 * | 3/2015 | Stoessel ................ | C07C 15/28 257/40 |
| 9,601,701 | B2 | 3/2017 | Miyashita et al. | |
| 2004/0076853 | A1 * | 4/2004 | Jarikov ................ | C09K 11/06 428/690 |
| 2006/0216633 | A1 * | 9/2006 | Kubota ................ | C07C 15/28 430/139 |

(Continued)

FOREIGN PATENT DOCUMENTS

| | | |
|---|---|---|
| CN | 101125794 A | 2/2008 |
| CN | 101415663 A | 4/2009 |

(Continued)

OTHER PUBLICATIONS

Cao et al., "Manganese (III) Acetate-Mediated Cyclization of Diarylmethylenecyclopropa[ ]naphthalenes: A Method for the Synthesis of 1,2-Benzanthracene Derivatives", Journal of Organic Chemistry, 2011, vol. 76, pp. 9329-9337.

(Continued)

*Primary Examiner* — Dawn L Garrett
(74) *Attorney, Agent, or Firm* — Faegre Drinker Biddle & Reath LLP

(57) ABSTRACT

The present application relates to a substituted benzanthracene compound of a formula (I) or (II). The application furthermore relates to an electronic device which comprises the said benzanthracene compound.

13 Claims, No Drawings

(56) References Cited

U.S. PATENT DOCUMENTS

| | | | | |
|---|---|---|---|---|
| 2007/0273272 | A1* | 11/2007 | Kubota | C07C 13/567 |
| | | | | 313/504 |
| 2010/0187505 | A1 | 7/2010 | Stoessel et al. | |
| 2011/0092701 | A1* | 4/2011 | Pflumm | C07C 211/61 |
| | | | | 544/247 |
| 2012/0112169 | A1* | 5/2012 | Mizuki | C07D 307/91 |
| | | | | 257/40 |
| 2012/0168735 | A1* | 7/2012 | Pflumm | H01L 51/5048 |
| | | | | 257/40 |

FOREIGN PATENT DOCUMENTS

| | | |
|---|---|---|
| CN | 101540375 A | 9/2009 |
| CN | 101679855 A | 3/2010 |
| CN | 102076640 A | 5/2011 |
| CN | 102076641 A | 5/2011 |
| CN | 102076645 A | 5/2011 |
| DE | 102007024850 A1 | 12/2008 |
| JP | 2010-528070 | 8/2010 |
| JP | 2013-510104 A | 3/2013 |
| JP | 2013-087072 A | 5/2013 |
| TW | 200914576 A | 4/2009 |
| WO | 2010/114256 A2 | 10/2010 |
| WO | 2011/054142 A2 | 5/2011 |

OTHER PUBLICATIONS

Fu et al., Organic Preparations and Procedures International, vol. 14 No. 3, 1982, pp. 169-175.

International Preliminary Report on Patentability received for PCT Patent Application No. PCT/EP2015/000587, dated Oct. 27, 2016, 11 pages (7 pages of English Translation and 4 pages of Original Document).

International Search Report and Written Opinion received for PCT Patent Application No. PCT/EP2015/000587, 13 pages (6 pages of English Translation and 7 pages of Original Document), dated 2015.

* cited by examiner

MATERIALS FOR ELECTRONIC DEVICES

RELATED APPLICATIONS

This application is a national stage entry, filed pursuant to 35 U.S.C. § 371, of PCT/EP2015/000587, filed Mar. 17, 2015, which claims the benefit of European Patent Application No. 14001391.3, filed Apr. 16, 2014, which is incorporated herein by reference in its entirety.

The present application relates to an electronic device which comprises a substituted benzanthracene compound.

The term electronic device in accordance with the present invention is generally taken to mean electronic devices which comprise organic materials. It is preferably taken to mean OLEDs.

The general structure and functional principle of OLEDs is known to the person skilled in the art and is described, inter alia, in U.S. Pat. No. 4,539,507, U.S. Pat. No. 5,151,629, EP 0676461 and WO 1998/27136.

Further improvements are necessary with regard to the performance data of the electronic devices, in particular in view of broad commercial use, for example in displays or as light sources. Of particular importance in this connection are the lifetime, the efficiency and the operating voltage of the electronic devices and the colour values achieved. It is also important, for certain applications, to have soluble compounds available. In particular in the case of blue-emitting OLEDs, there is potential for improvement with respect to the lifetime of the devices and the colour values of the emitted light.

An important starting point for achieving the said improvements is the choice of the compound employed as matrix in the emitting layer of the electronic device, preferably in combination with a fluorescent emitter compound.

A matrix (or matrix compound or matrix material) in the emitting layer is, for the purposes of the present application, taken to mean compounds that are present in the emitting layer of the electronic device, but are not emitter compounds, i.e. are not or not significantly involved in the light emission by the emitting layer.

Emitter compounds are correspondingly taken to mean compounds of the emitting layer which emit light on operation of the electronic device. The term fluorescent emitters in accordance with the present application encompasses compounds in which the light emission takes place from a singlet state.

A multiplicity of compounds are described in the prior art as matrix compounds for use in the emitting layer. Examples thereof are anthracenes having aryl substituents in the 2-, 6-, 9- and 10-position, as described, for example, in WO 2007/110129, bisanthracene compounds, as described, for example, in WO 2007/065678, or anthracene compounds having substituents which are different from one another in the 9- and 10-position, as described, for example, in EP 1 553154.

The prior art furthermore describes benzanthracene compounds having a certain substitution patter for this use, for example in WO 2008/145239. The benzanthracene compounds disclosed therein are characterised in that they carry an aryl or heteroaryl group in one of positions 2, 3, 4, 5 or 6, and otherwise have no further substituents, in particular no substituents in positions 7 and 12.

Although the compounds disclosed in WO 2008/145239 have very good properties, there continues to be, however, a need for improvement. There is particular interest here in the development of novel compounds which facilitate deep-blue colour coordinates of the emitted light and/or a longer lifetime of the electronic device. Furthermore, it is of considerable interest for certain applications to have available compounds having improved solubility in common organic solvents, in particular in solvents which are employed in printing processes or spin-coating processes for the production of electronic devices.

There is also interest in novel compounds which can serve as alternatives to the compounds known from the prior art. Desirable uses of the compounds are not restricted to the use as matrix, but also include the use as, for example, electron-transport material, hole-transport material or emitter. In investigations on novel compounds for use in electronic devices, it has now been found, unexpectedly, that benzanthracene compounds having a defined substitution pattern of the following formula (I) or (II) are eminently suitable for use in electronic devices. In particular, they achieve one or more, preferably all, of the above-mentioned technical objects of provision of OLEDs having deep-blue colour coordinates of the emitted light, provision of OLEDs having a long lifetime and provision of compounds having good solubility in organic solvents.

The invention thus relates to a compound of a formula (I) or (II)

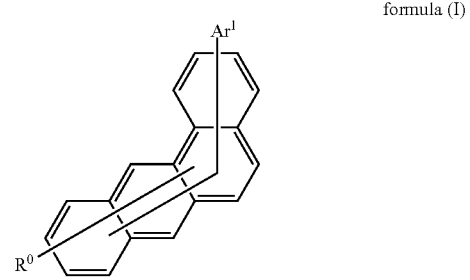

formula (I)

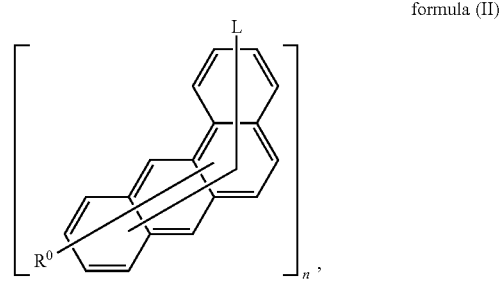

formula (II)

where the following applies to the symbols occurring:

Ar$^1$ is selected from aromatic ring systems having 6 to 40 aromatic ring atoms, which may be substituted by one or more radicals R$^2$, or heteroaromatic ring systems having 5 to 40 aromatic ring atoms, which may be substituted by one or more radicals R$^2$;

R$^0$ is C(=O)R$^3$, CN, Si(R$^3$)$_3$, P(=O)(R$^3$)$_2$, OR$^3$, S(=O)R$^3$, S(=O)$_2$R$^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^3$ and where one or more CH$_2$ groups in the above-mentioned groups may be replaced by —R$^3$C=CR$^3$—, —C≡C—, Si(R$^3$)$_2$, C=O, C=NR$^3$, —C(=O)O—, —C(=O)NR$^3$—, NR$^3$, P(=O)(R$^3$), —O—, —S—, SO or SO$_2$; a radical R$^0$ may be linked to a radical R$^1$ and may form a ring;

L is an n-valent group selected from aromatic ring systems having 6 to 40 aromatic ring atoms, which may be substituted by one or more radicals $R^2$, or from heteroaromatic ring systems having 5 to 40 aromatic ring atoms, which may be substituted by one or more radicals $R^2$; or L is a chemical bond, where n is then equal to 2;

$R^1$, $R^2$ are on each occurrence, identically or differently, H, D, F, C(=O)$R^3$, CN, Si($R^3$)$_3$, N($R^3$)$_2$, P(=O)($R^3$)$_2$, O$R^3$, S(=O)$R^3$, S(=O)$_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —$R^3$C=C$R^3$—, —C≡C—, Si($R^3$)$_2$, C=O, C=N$R^3$, —C(=O)O—, —C(=O)N$R^3$—, N$R^3$, P(=O)($R^3$), —O—, —S—, SO or SO$_2$, or an aromatic ring system having 6 to 40 aromatic ring atoms, which may be substituted by one or more radicals $R^3$, or a heteroaromatic ring system having 5 to 40 aromatic ring atoms, which may be substituted by one or more radicals $R^3$; two or more radicals $R^1$ or $R^2$ may be linked to one another and may form a ring;

$R^3$ is on each occurrence, identically or differently, H, D, F, C(=O)$R^4$, CN, Si($R^4$)$_3$, N($R^4$)$_2$, P(=O)($R^4$)$_2$, O$R^4$, S(=O)$R^4$, S(=O)$_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more CH$_2$ groups in the above-mentioned groups may be replaced by —$R^4$C=C$R^4$—, —C≡C—, Si($R^4$)$_2$, C=O, C=N$R^4$, —C(=O)O—, —C(=O)N$R^4$—, N$R^4$, P(=O)($R^4$), —O—, —S—, SO or SO$_2$, or an aromatic ring system having 6 to 40 aromatic ring atoms, which may be substituted by one or more radicals $R^4$, or a heteroaromatic ring system having 5 to 40 aromatic ring atoms, which may be substituted by one or more radicals $R^4$; two or more radicals $R^3$ may be linked to one another and may form a ring;

$R^4$ is on each occurrence, identically or differently, H, D, F, CN or an aliphatic, aromatic or heteroaromatic organic radical having 1 to 20 C atoms, in which, in addition, one or more H atoms may be replaced by D, F or CN; two or more substituents $R^4$ may be linked to one another and may form a ring;

n is equal to 2, 3, 4, 5 or 6;

where the compound of the formula (I) or (II) may contain a radical $R^1$ at each of the positions indicated as unsubstituted; and where the following compounds are excluded:

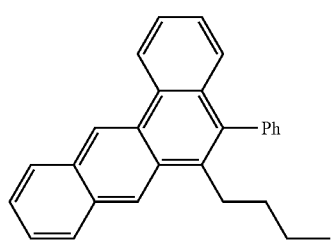

-continued

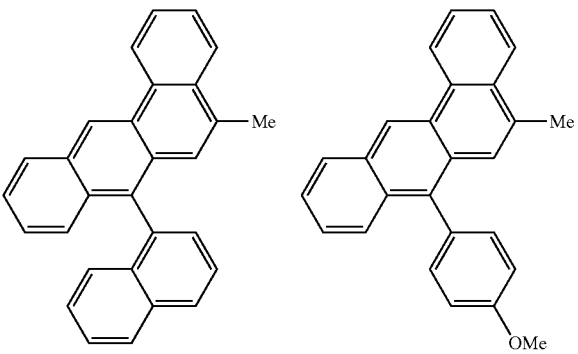

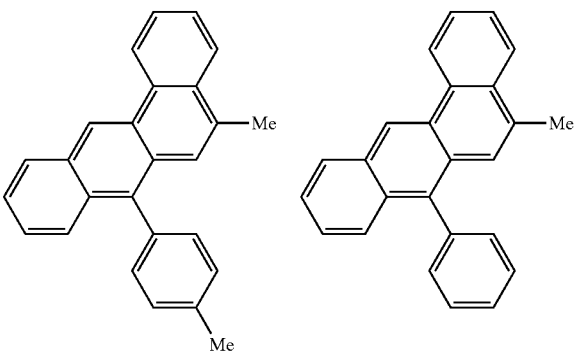

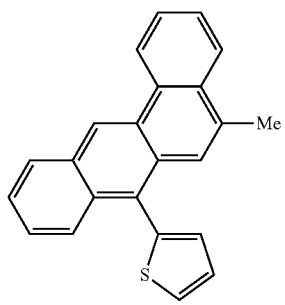

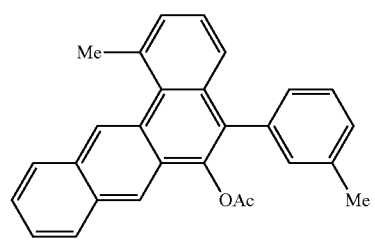

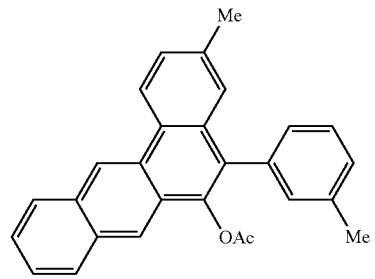

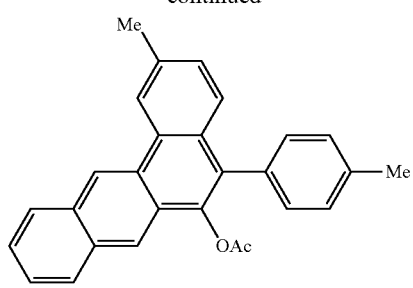

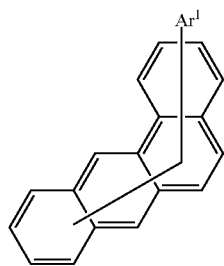

The graphic representation

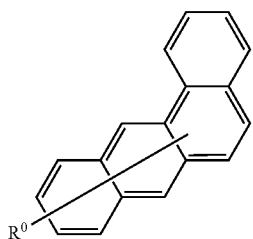

means that a group Ar¹ is bonded at any desired position selected from positions 1 to 12 of the benzanthracene.

The same applies to the representation of the group L in formula (II).

The graphic representation

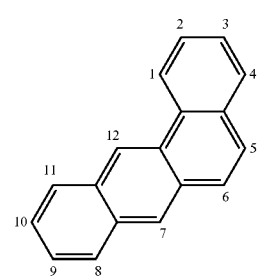

means that a group R⁰ is bonded at a position selected from positions 5, 6, 7, 8, 9, 10, 11 or 12 of the benzanthracene.

In the present application, the following numbering of the positions of the benzanthracene structure is used:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, nbutylthio, i-butylthio, s-butylthio, t-butylthio, n-pentylthio, s-pentylthio, nhexylthio, cyclohexythio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. Furthermore, however, the above-mentioned formulation is also intended to be taken to mean that, in the case where one of the two radicals represents hydrogen, the second radical is bonded at the position to which the hydrogen atom was bonded, with formation of a ring.

For the compound of the formula (I), the group Ar$^1$ is preferably not present in position 7. It is furthermore preferred for formula (I) or (II) for no group R$^1$ which is selected from aromatic or heteroaromatic ring systems to be present in position 7. It is most preferred for formula (I) or (II) for either a group R$^1$ which is selected from H and D, and is preferably H, to be present in position 7 or for a group R$^0$ to be present in position 7. The preferred embodiments indicated for group R$^0$ apply here.

The compound of the formula (I) preferably contains at least one condensed aryl group, preferably at least one condensed aryl group having 14 to 18 aromatic ring atoms, in addition to the benzanthracene skeleton. The condensed aryl group can optionally be present as group Ar$^1$, R$^1$, R$^2$, R$^3$ or R$^4$, preferably as group Ar$^1$ or R$^2$. In accordance with its occurrence as group Ar$^1$, R$^1$, R$^2$, R$^3$ or R$^4$ in the formula (I), it may be substituted as allowed for the relevant group. For example, if it is present as a group Ar$^1$, it may be substituted by one or more radicals R$^2$.

The group Ar$^1$ is preferably present in a position of the benzanthracene selected from positions 1, 2, 3, 4, 5, 6, 8, 9, 10, 11, 12, particularly preferably in a position selected from positions 2, 3, 4, 5, 6, 8, 9, 10, 11, very particularly preferably in a position selected from positions 2, 3, 4, 5, 6, 8, 11, even more preferably in a position selected from positions 2, 3, 4, 5, 6, and most preferably in a position selected from positions 4 and 5.

The group L is preferably present in a position of the benzanthracene selected from positions 1, 2, 3, 4, 5, 6, 8, 9, 10, 11, 12, particularly preferably in a position selected from positions 2, 3, 4, 5, 6, 8, 9, 10, 11, very particularly preferably in a position selected from positions 2, 3, 4, 5, 6, 8, 11, even more preferably in a position selected from positions 2, 3, 4, 5, 6, and most preferably in a position selected from positions 4 and 5.

The group R$^0$ is preferably present in a position of the benzanthracene selected from positions 7, 8, 9, 10, 11, 12, particularly preferably in a position selected from positions 7 and 12, very particularly preferably in position 7.

The compound of the formula (I) or (II) preferably contains not more than three radicals R$^1$, particularly preferably not more than two radicals $R^1$, very particularly preferably precisely one or no radical $R^1$, and most preferably no radical $R^1$.

$Ar^1$ is preferably selected from aromatic ring systems having 6 to 30 aromatic ring atoms, which may be substituted by one or more radicals $R^2$, and heteroaromatic ring systems having 5 to 30 aromatic ring atoms, which may be substituted by one or more radicals $R^2$. $Ar^1$ is particularly preferably selected on each occurrence, identically or differently, from aromatic ring systems having 6 to 25 aromatic ring atoms, which may be substituted by one or more radicals $R^2$. $Ar^1$ is particularly preferably selected from the group consisting of benzene, naphthalene, anthracene, benzanthracene, phenanthrene, benzophenanthrene, pyrene, chrysene, perylene, fluoranthene, naphthacene, pentacene, benzopyrene, biphenyl, terphenyl, quaterphenyl, fluorene, spirobifluorene, furan, benzofuran, isobenzofuran, dibenzofuran, thiophene, benzothiophene, isobenzothiophene, dibenzothiophene, Indole, isoindole, carbazole, indolocarbazole, indenocarbazole, pyridine, quinoline, isoquinoline, acridine, phenanthridine, benzimidazole, pyrimidine, pyrazine and triazine, where the said groups may each be substituted by one or more radicals $R^2$.

Preference is given to radicals $R^2$, which are bonded to groups $Ar^1$, selected from H, D, F, CN, straight-chain alkyl or alkoxy groups having 1 to 10 C atoms and branched or cyclic alkyl or alkoxy groups having 3 to 10 C atoms, where the above-mentioned groups may each be substituted by one or more radicals $R^3$, and from aromatic ring systems having 6 to 24 aromatic ring atoms, which may be substituted by one or more radicals $R^3$, and from heteroaromatic ring systems having 5 to 24 aromatic ring atoms, which may be substituted by one or more radicals $R^3$. The aromatic ring systems having 6 to 24 aromatic ring atoms, which may be substituted by one or more radicals $R^3$, and the heteroaromatic ring systems having 5 to 24 aromatic ring atoms, which may be substituted by one or more radicals $R^3$, are preferably selected here from the group consisting of benzene, naphthalene, anthracene, benzanthracene, phenanthrene, benzophenanthrene, pyrene, chrysene, perylene, fluoranthene, naphthacene, pentacene, benzopyrene, biphenyl, terphenyl, quaterphenyl, fluorene, spirobifluorene, furan, benzofuran, isobenzofuran, dibenzofuran, thiophene, benzothiophene, isobenzothiophene, dibenzothiophene, indole, isoindole, carbazole, indolocarbazole, indenocarbazole, pyridine, quinoline, isoquinoline, acridine, phenanthridine, benzimidazole, pyrimidine, pyrazine and triazine, where the said groups may each be substituted by one or more radicals $R^3$.

Preferred embodiments of the group $Ar^1$ conform to the following formulae $(Ar^1\text{-}1)$ to $(Ar^1\text{-}6)$:

$*-Ar^2$  formula $(Ar^1\text{-}1)$

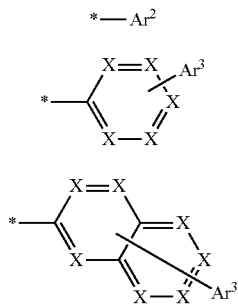

formula $(Ar^1\text{-}2)$ formula $(Ar^1\text{-}3)$

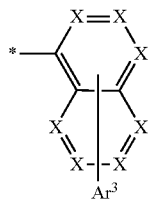

formula $(Ar^1\text{-}4)$

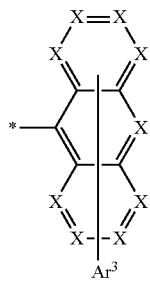

formula $(Ar^1\text{-}5)$

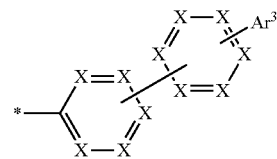

formula $(Ar^1\text{-}6)$ where:

X is selected on each occurrence, identically or differently, from the group comprising N, $CR^2$ and C, where X may only be equal to C if a group $Ar^3$ is bonded to X;

$Ar^2$ is selected from aromatic ring systems having 6 to 30 aromatic ring atoms, which may be substituted by one or more radicals $R^2$, and from heteroaromatic ring systems having 5 to 30 aromatic ring atoms, which may be substituted by one or more radicals $R^2$;

$Ar^3$ is selected from aromatic ring systems having 6 to 24 aromatic ring atoms, which may be substituted by one or more radicals $R^3$, and from heteroaromatic ring systems having 5 to 24 aromatic ring atoms, which may be substituted by one or more radicals $R^3$;

and the bond labelled with * is the bonding position of the group to the benzanthracene unit.

Corresponding to the formulae $(Ar^1\text{-}3)$, $(Ar^1\text{-}4)$ and $(Ar^1\text{-}5)$, the group $Ar^3$ is in each case bonded in any desired free position of the naphthyl derivative or of the anthracenyl derivative. Bonding in the 9- or 10-position of the anthracenyl derivative is preferred for formula $(Ar^1\text{-}5)$.

The group X is preferably selected from the group comprising $CR^2$ and C, where X may only be equal to C if a group $Ar^3$ is bonded to X.

$Ar^2$ is preferably selected from condensed aryl groups having 10 to 22 aromatic ring atoms, which may be substituted by one or more radicals $R^2$, and from condensed heteroaryl groups having 9 to 22 aromatic ring atoms, which may be substituted by one or more radicals $R^2$. $Ar^2$ is particularly preferably selected from the group consisting of naphthalene, anthracene, benzanthracene, phenanthrene, benzophenanthrene, pyrene, chrysene, perylene, fluoranthene, naphthacene, pentacene, benzopyrene, benzofuran, isobenzofuran, dibenzofuran, benzothiophene, isobenzothiophene, dibenzothiophene, indole, isoindole, carbazole, quinoline, isoquinoline, acridine, phenanthridine, benzimidazole, where the said groups may each be substituted by one or more radicals $R^2$. $Ar^2$ is very particularly preferably selected from the group consisting of naphthalene, anthracene, benzanthracene, phenanthrene, benzophenanthrene, pyrene, chrysene, perylene, fluoranthene and naphthacene, where the said groups may each be substituted by one or more radicals $R^2$.

$Ar^3$ is preferably selected from aryl groups having 6 to 22 aromatic ring atoms, which may be substituted by one or more radicals $R^3$, and from heteroaryl groups having 5 to 22 aromatic ring atoms, which may be substituted by one or more radicals $R^3$. $Ar^3$ is particularly preferably selected from the group consisting of benzene, naphthalene, anthracene, benzanthracene, phenanthrene, benzophenanthrene, pyrene, chrysene, perylene, fluoranthene, naphthacene, pentacene, benzopyrene, benzofuran, isobenzofuran, dibenzofuran, benzothiophene, isobenzothiophene, dibenzothiophene, indole, isoindole, carbazole, quinoline, isoquinoline, acridine, phenanthridine, benzimidazole, where the said groups may each be substituted by one or more radicals $R^3$. $Ar^3$ is very particularly preferably selected from the group consisting of benzene, naphthalene, anthracene, benzanthracene, phenanthrene, benzophenanthrene, pyrene, chrysene, perylene, fluoranthene and naphthacene, where the said groups may each be substituted by one or more radicals $R^3$.

Preferred embodiments of the group $Ar^1$ of the formula ($Ar^1$-1) conform to the following formulae ($Ar^1$-1-1) to ($Ar^1$-1-8):

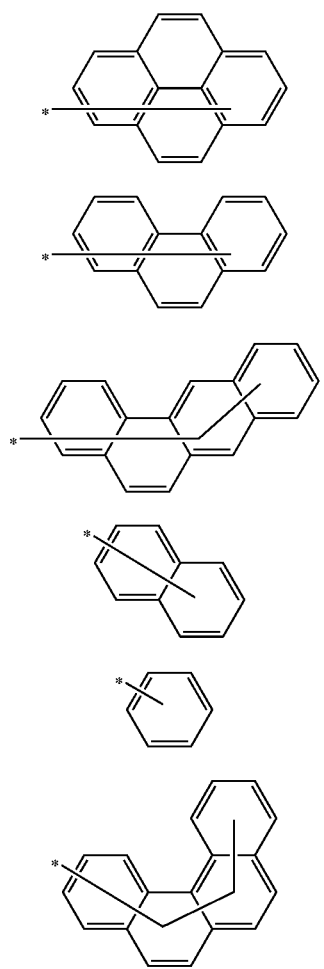

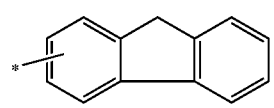

formula ($Ar^1$-1-7)

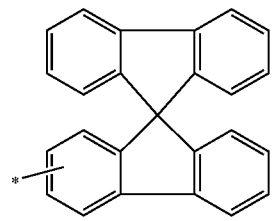

formula ($Ar^1$-1-8)

where:
radicals $R^2$ may in each case be present at free positions; and
the bond labelled with * is the bonding position of the group to the benzanthracene unit.

Preferred embodiments of the group $A^1$ of the formula ($Ar^1$-2) conform to the following formulae ($Ar^1$-2-1) to ($Ar^1$-2-6):

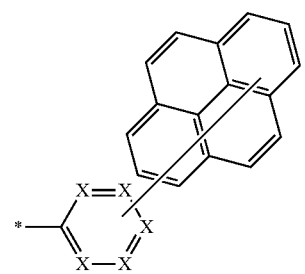

formula ($Ar^1$-2-1)

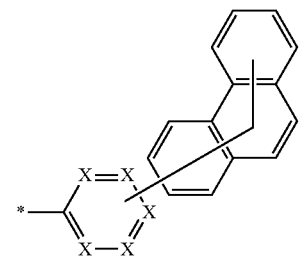

formula ($Ar^1$-2-2)

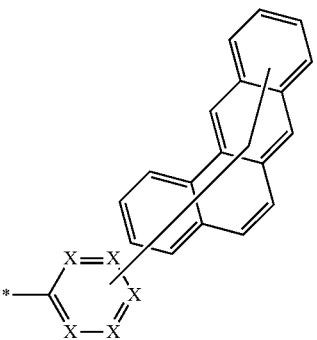

formula ($Ar^1$-2-3)

formula (Ar¹-2-4)

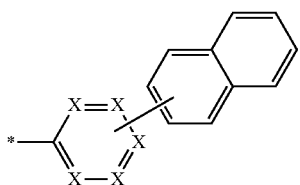

formula (Ar¹-2-5)

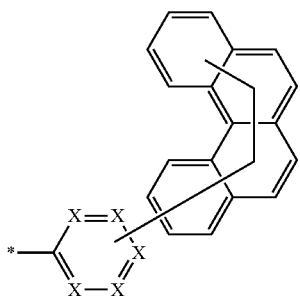

formula (Ar¹-2-6)

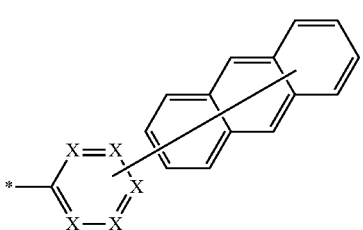

where:

X is defined as above, and is preferably selected on each occurrence, identically or differently, from CR² and C, where X may only be C if a substituent is bonded to X;

radicals R³ may in each case be present at free positions; and the bond labelled with * is the bonding position of the group to the benzanthracene unit.

Preferred embodiments of the group Ar¹ of the formula (Ar¹-5) conform to the following formulae (Ar¹-5-1) to (Ar¹-5-7):

formula (Ar¹-5-1)

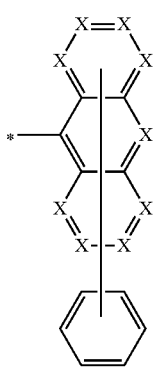

formula (Ar¹-5-2)

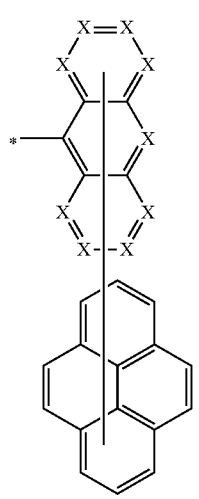

formula (Ar¹-5-3)

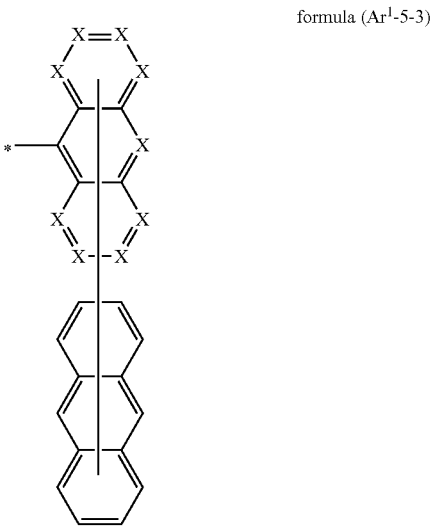

(Ar¹-5-4)

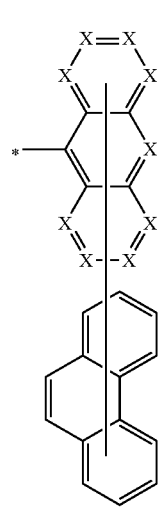

-continued

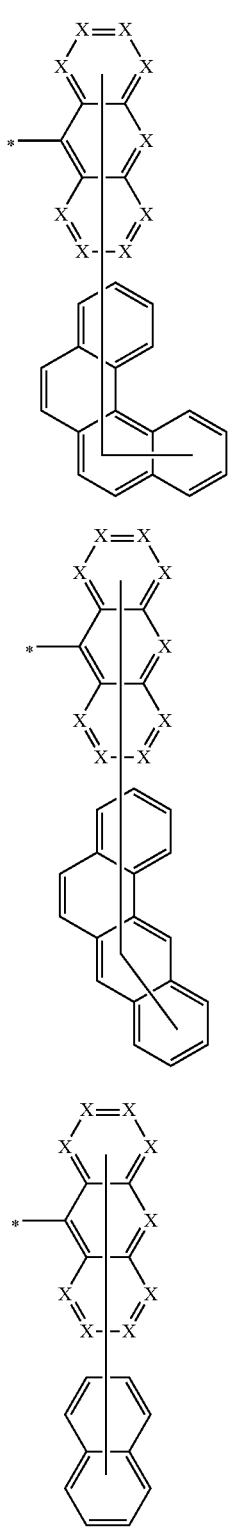

(Ar¹-5-5)

(Ar¹-5-6)

formula (Ar¹-5-7)

where:
X is defined as above, and is preferably selected on each occurrence, identically or differently, from CR² and C, where X may only be C if a substituent is bonded to X; radicals R³ may in each case be present at free positions; and the bond labelled with * is the bonding position of the group to the benzanthracene unit.

Preferred embodiments of the group Ar¹ of the formula (Ar¹-6) conform to the following formulae (Ar¹-6-1) to (Ar¹-6-6):

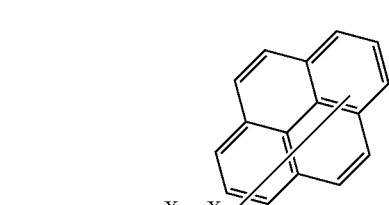

formula (Ar¹-6-1)

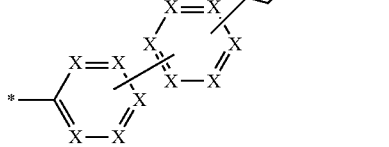

formula (Ar¹-6-2)

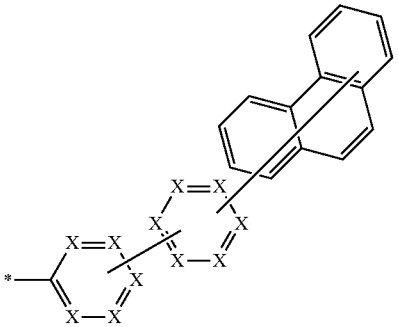

formula (Ar¹-6-3)

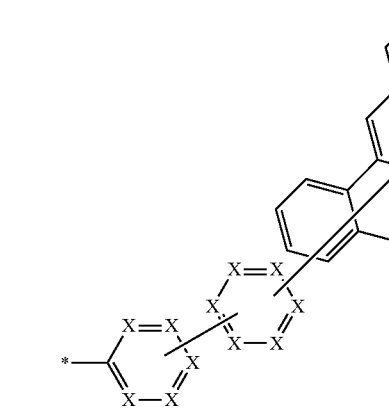

formula (Ar¹-6-4)

-continued formula (Ar¹-6-5)

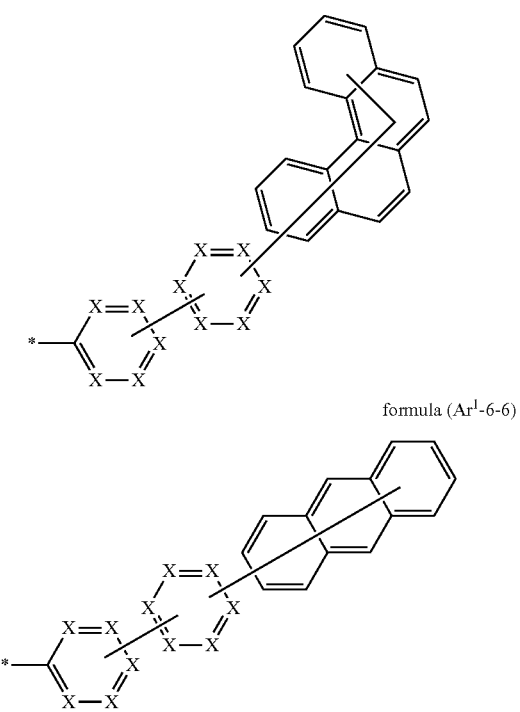

formula (Ar¹-6-6)

where:
X is defined as above, and is preferably selected on each occurrence, identically or differently, from $CR^2$ and C, where X may only be C if a substituent is bonded to X; radicals $R^3$ may in each case be present at free positions; and the bond labelled with * is the bonding position of the group to the benzanthracene unit.

$R^0$ is preferably selected from $C(=O)R^3$, CN, $Si(R^3)_3$, $OR^3$, straight-chain alkyl or alkoxy groups having 1 to 10 C atoms or branched or cyclic alkyl or alkoxy groups having 3 to 10 C atoms or alkenyl or alkynyl groups having 2 to 10 C atoms, where the above-mentioned groups may each be substituted by one or more radicals $R^3$, and where one or more $CH_2$ groups in the above-mentioned groups may be replaced by —$R^3C=CR^3$—, —C≡C—, $Si(R^3)_2$, —O— or —S—. $R^0$ is particularly preferably selected from $Si(R^3)_3$, straight-chain alkyl or alkoxy groups having 1 to 10 C atoms or branched or cyclic alkyl or alkoxy groups having 3 to 10 C atoms, where the above-mentioned groups may each be substituted by one or more radicals $R^3$. $R^0$ is very particularly preferably selected from methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cydoheptyl, n-octyl, cydooctyl, 2-ethylhexyl, methoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy and 2-ethylhexyloxy, trimethylsilyl, triethylsilyl, and derivatives of the above-mentioned radicals which are substituted by radicals —Si$(R^4)_3$.

L is preferably selected from aromatic ring systems having 6 to 30 aromatic ring atoms, which may be substituted by one or more radicals $R^2$, or from heteroaromatic ring systems having 5 to 30 aromatic ring atoms, which may be substituted by one or more radicals $R^2$, or L is a single bond, where in this case n is equal to 2. L is particularly preferably selected from benzene, naphthalene, anthracene, benzanthracene, phenanthrene, benzophenanthrene, pyrene, chrysene, perylene, fluoranthene, naphthacene, pentacene, benzopyrene, biphenyl, terphenyl, quaterphenyl, fluorene, spirobifluorene, furan, benzofuran, isobenzofuran, dibenzofuran, thiophene, benzothiophene, isobenzothiophene, dibenzothiophene, indole, isoindole, carbazole, indolocarbazole, indenocarbazole, pyridine, quinoline, isoquinoline, acridine, phenanthridine, benzimidazole, pyrimidine, pyrazine and triazine, where the said groups may each be substituted by one or more radicals $R^2$, or L is a single bond, where in this case n is equal to 2.

Index n is preferably equal to 2 or 3, particularly preferably equal to 2.

$R^1$ is preferably selected on each occurrence, identically or differently, from H, D, F, CN, $Si(R^3)_3$, $N(R^3)_2$, straight-chain alkyl or alkoxy groups having 1 to 10 C atoms and branched or cyclic alkyl or alkoxy groups having 3 to 10 C atoms, where the above-mentioned groups may each be substituted by one or more radicals $R^3$ and where one or more $CH_2$ groups in the above-mentioned groups may be replaced by —C≡C—, —$R^3C=CR^3$—, $Si(R^3)_2$, C=O, C=$NR^3$, —$NR^3$—, —O—, —S—, —C(=O)O— or —C(=O)$NR^3$—, and aromatic ring systems having 6 to 24 aromatic ring atoms, which may be substituted by one or more radicals $R^3$, and heteroaromatic ring systems having 5 to 24 aromatic ring atoms, which may be substituted by one or more radicals $R^3$. $R^1$ is particularly preferably selected on each occurrence, identically or differently, from H, D, F, CN, $Si(R^3)_3$, straight-chain alkyl or alkoxy groups having 1 to 10 C atoms and branched or cyclic alkyl or alkoxy groups having 3 to 10 C atoms, where the above-mentioned groups may each be substituted by one or more radicals $R^3$.

$R^2$ is preferably selected on each occurrence, identically or differently, from H, D, F, CN, $Si(R^3)_3$, $N(R^3)_2$, straight-chain alkyl or alkoxy groups having 1 to 10 C atoms and branched or cyclic alkyl or alkoxy groups having 3 to 10 C atoms, where the above-mentioned groups may each be substituted by one or more radicals $R^3$ and where one or more $CH_2$ groups in the above-mentioned groups may be replaced by —C≡C—, —$R^3C=CR^3$—, $Si(R^3)_2$, C=O, C=$NR^3$, —$NR^3$—, —O—, —S—, —C(=O)O— or —C(=O)$NR^3$—, and aromatic ring systems having 6 to 24 aromatic ring atoms, which may be substituted by one or more radicals $R^3$, and heteroaromatic ring systems having 5 to 24 aromatic ring atoms, which may be substituted by one or more radicals $R^3$.

$R^3$ is preferably selected on each occurrence, identically or differently, from H, D, F, CN, $Si(R^4)_3$, $N(R^4)_2$, straight-chain alkyl or alkoxy groups having 1 to 10 C atoms and branched or cyclic alkyl or alkoxy groups having 3 to 10 C atoms, where the above-mentioned groups may each be substituted by one or more radicals $R^4$ and where one or more $CH_2$ groups in the above-mentioned groups may be replaced by —C≡C—, —$R^4C=CR^4$—, $Si(R^4)_2$, C=O, C=$NR^4$, —$NR^4$—, —O—, —S—, —C(=O)O— or —C(=O)$NR^4$—, and aromatic ring systems having 6 to 24 aromatic ring atoms, which may be substituted by one or more radicals $R^4$, and heteroaromatic ring systems having 5 to 24 aromatic ring atoms, which may be substituted by one or more radicals $R^4$.

Preferred embodiments of the compound of the formulae (I) and (II) conform to the formulae (I-1) and (I-2) and (II-1) and (II-2)

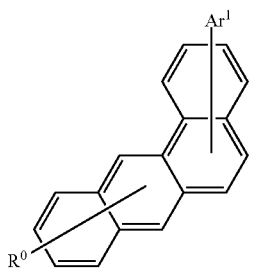

formula (I-1)

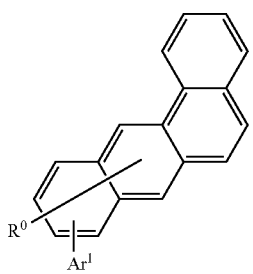

formula (I-2)

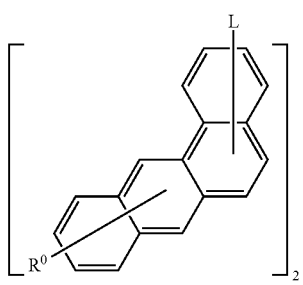

formula (II-1)

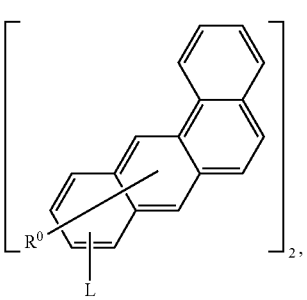

formula (II-2)

where the groups L, R⁰ and Ar¹ occurring are defined as above, and where groups R¹, as defined above, may in each case be present in all positions of the benzanthracene indicated as unsubstituted.

In accordance with the indication in formula (I-1), the group Ar¹ in formula (I-1) is bonded in a position selected from positions 1, 2, 3, 4, 5, 6. Preference is given here to a position selected from positions 2, 4, 5, particularly preferably a position selected from positions 4 and 5.

In accordance with the indication in formula (II-1), the group L in formula (II-1) is bonded in a position selected from positions 1, 2, 3, 4, 5, 6. Preference is given here to a position selected from positions 2, 4, 5, particularly preferably a position selected from positions 4 and 5.

In accordance with the indication in formulae (I-1) and (II-1), the group R⁰ in formulae (I-1) and (II-1) is bonded in a position selected from positions 7, 8, 9, 10, 11, 12. Preference is given here to a position selected from positions 7 and 12, particularly preferably position 7.

In accordance with the indication in formula (I-2), the group Ar¹ in formula (I-2) is bonded in a position selected from positions 8, 9, 10, 11.

In accordance with the indication in formula (II-2), the group L in formula (II-2) is bonded in a position selected from positions 8, 9, 10, 11.

In accordance with the indication in formulae (I-2) and (II-2), the group R⁰ in formulae (I-2) and (II-2) is bonded in a position selected from positions 7, 8, 9, 10, 11, 12. Preference is given here to a position selected from positions 7 and 12, particularly preferably position 7.

The preferred embodiments indicated above of the radicals L, Ar¹, R⁰, R¹, R² and R³ are likewise preferred for formulae (I-1), (I-2), (II-1) and (II-2).

Of the formulae (I-1), (I-2), (II-1) and (II-2), particular preference is given to the formula (I-1).

Preferred embodiments of the compound of the formula (I) conform to the formulae (I-1-1) and (I-2-1)

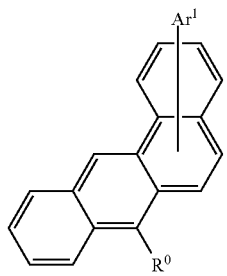

formula (I-1-1)

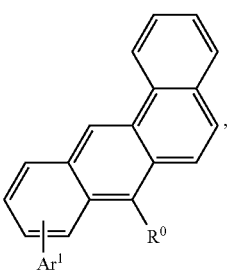

formula (I-2-1)

where the groups R⁰ and Ar¹ occurring are defined as above, and where groups R¹, as defined above, may in each case be present in all positions of the benzanthracene indicated as unsubstituted.

The preferred embodiments indicated above of the radicals Ar¹, R⁰, R¹, R² and R³ are likewise preferred for formulae (I-1-1) and (I-2-1).

In accordance with the indication in formula (I-1-1), the group Ar¹ in formula (I-1-1) is bonded in a position selected from positions 1, 2, 3, 4, 5, 6. It is preferred for formula (I-1-1) for the group Ar¹ to be bonded in a position selected from positions 2, 4 and 5, particularly preferably in a position selected from positions 4 and 5.

In accordance with the indication in formula (I-2-1), the group Ar¹ in formula (I-2-1) is bonded in a position selected from positions 8, 9, 10, 11.

Of the formulae (I-1-1) and (I-2-1), particular preference is given to the formula (I-1-1).

The following compounds are examples of compounds of the formula (I) or (II):

1
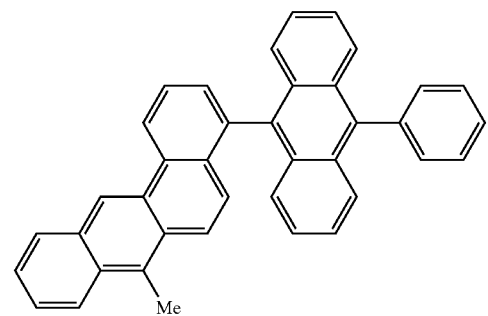
2
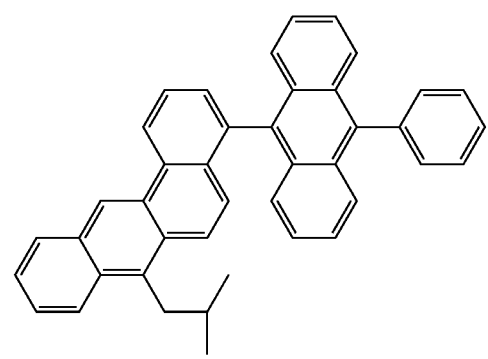
3
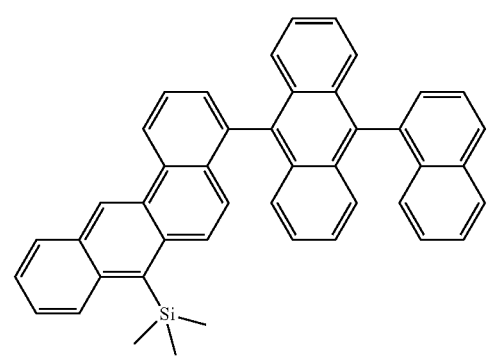
4
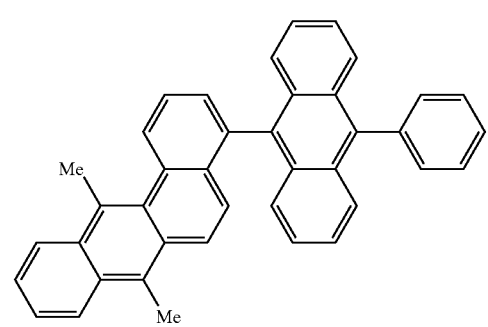
5
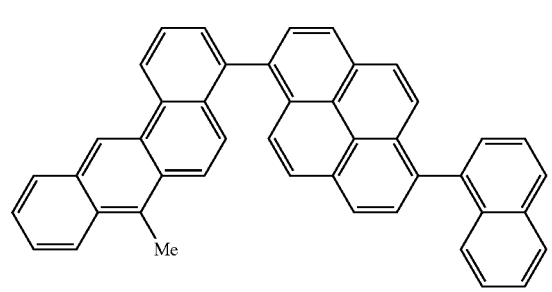
6
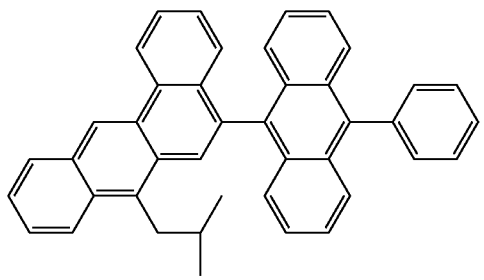
7
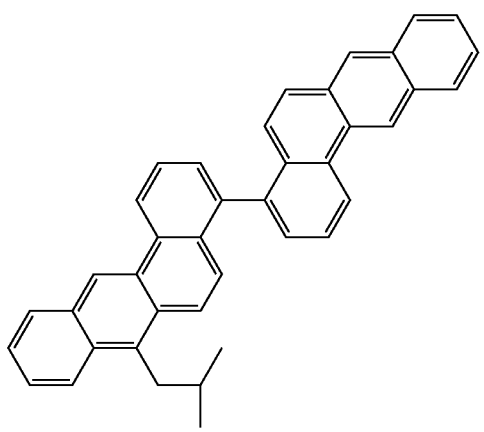
8
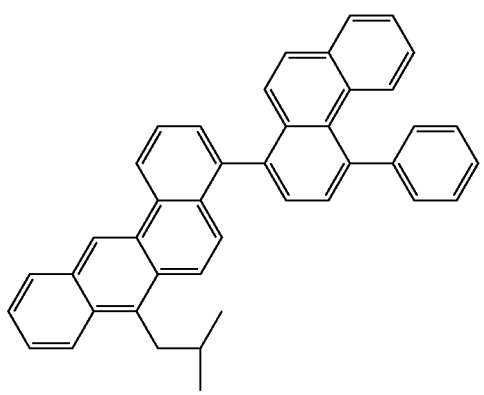
9
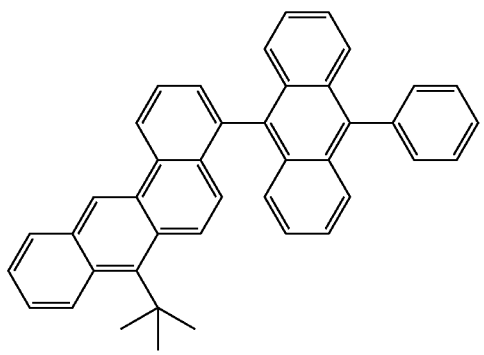

10
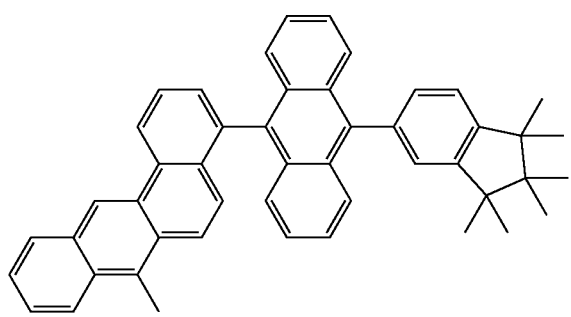
11
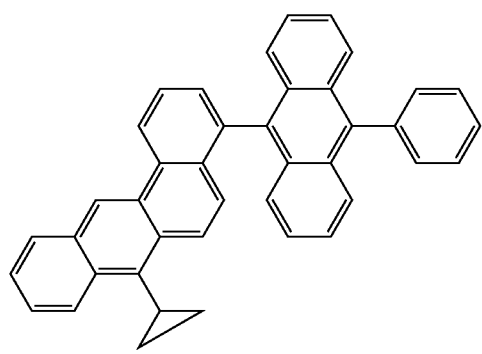
12
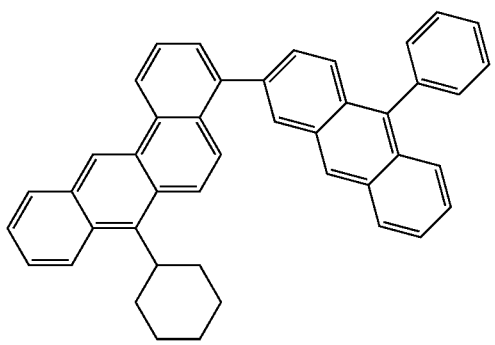
13
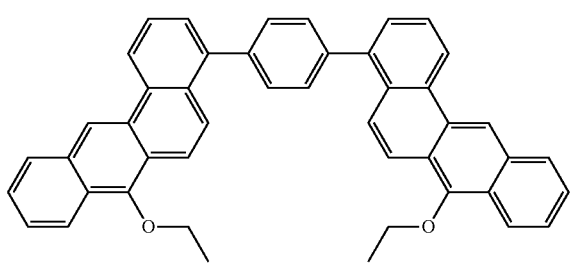
14
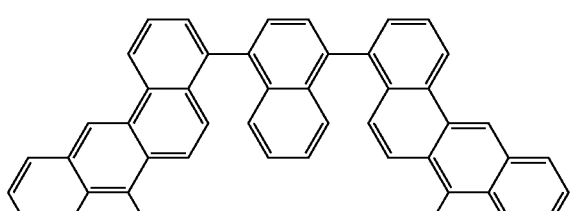
15
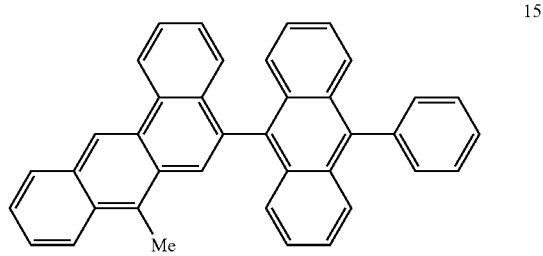
16
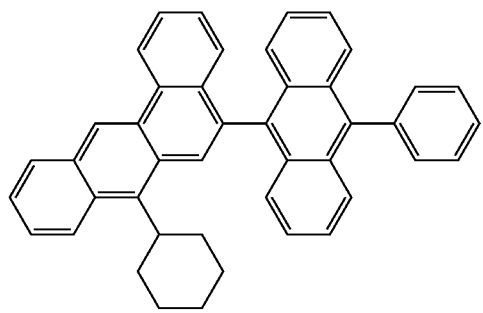
17
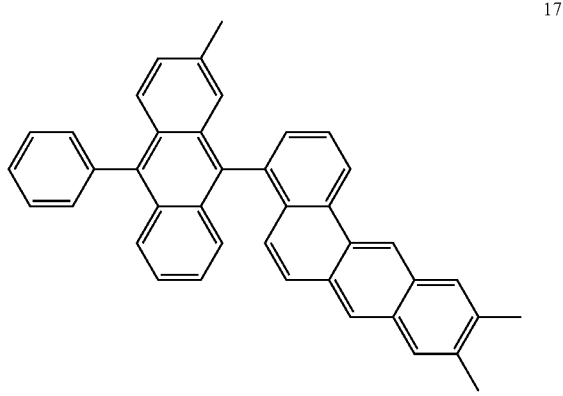
18
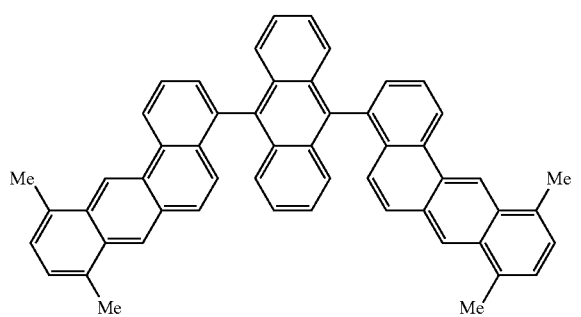
19
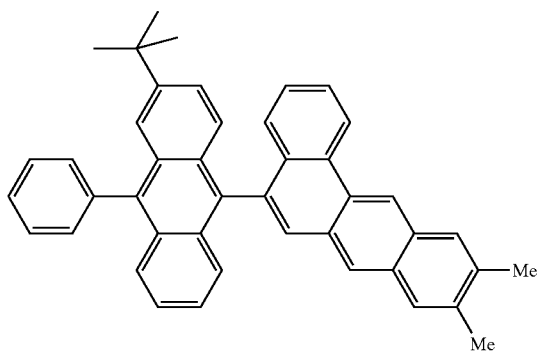

20
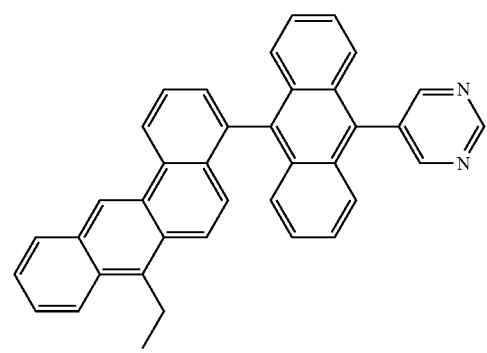
21
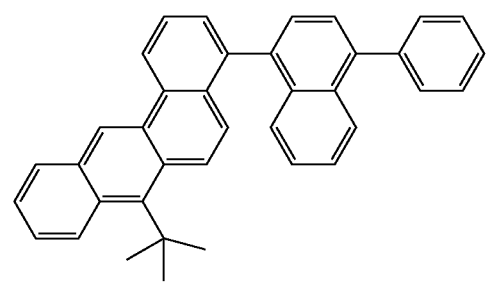
22
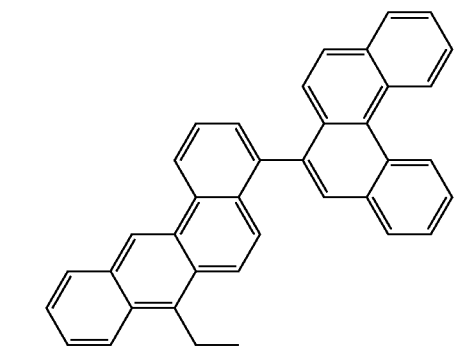
23
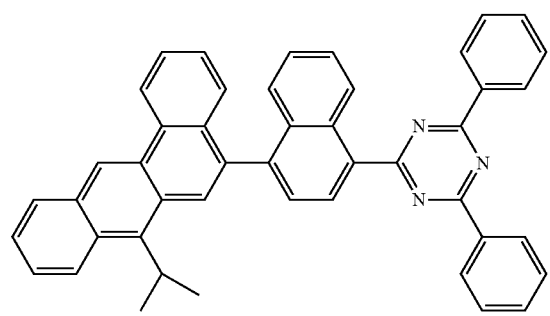
24
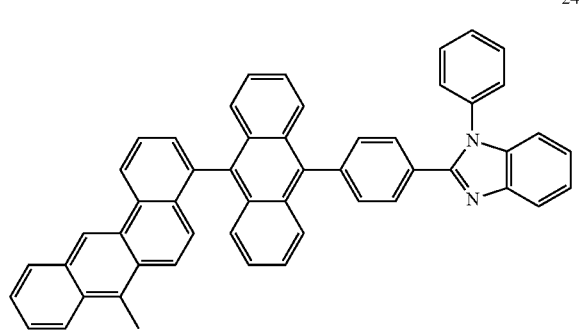
25
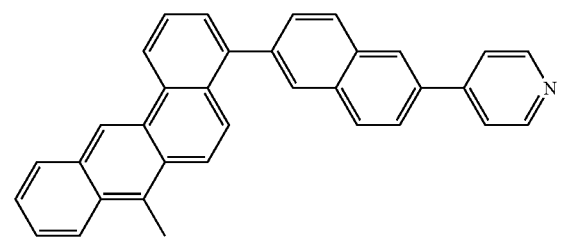
26
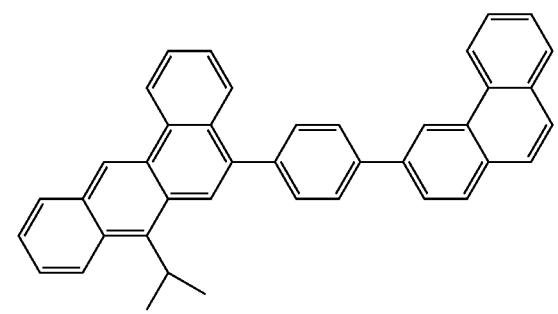
27
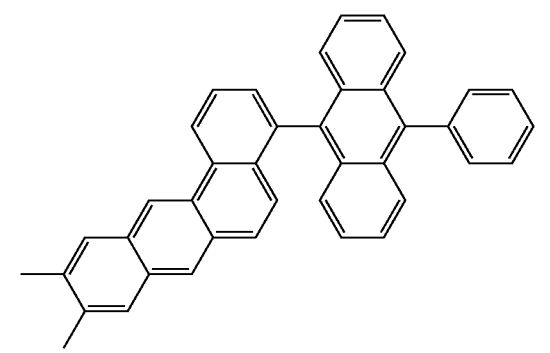
28
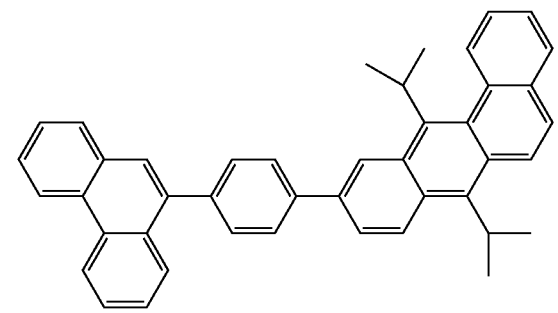
29
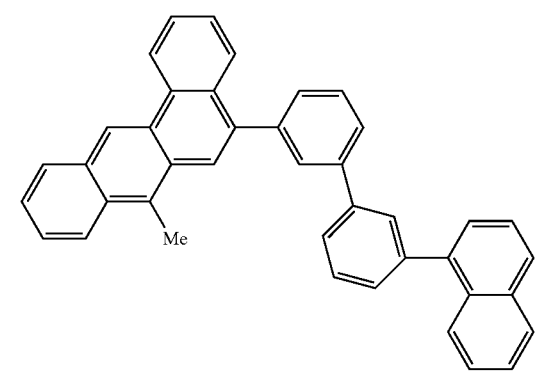

30
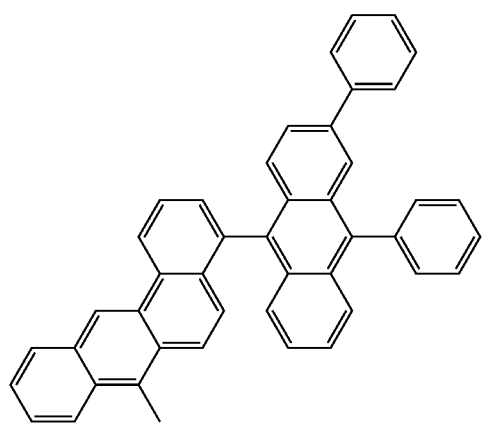
31
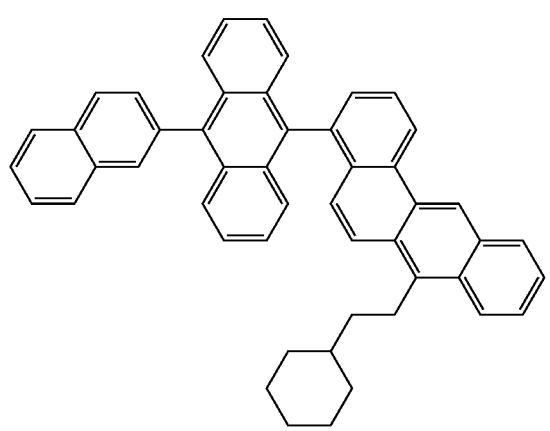
32
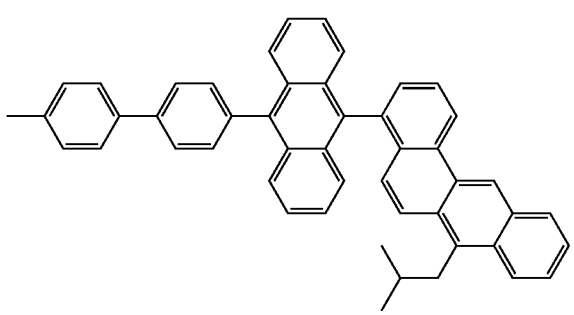
33
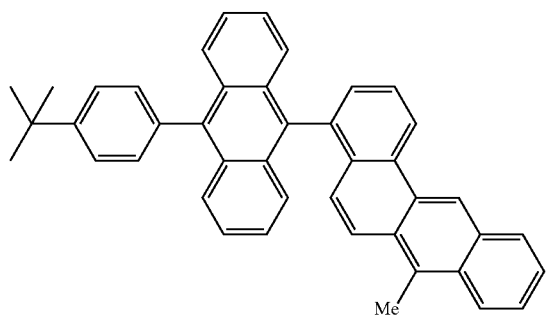
34
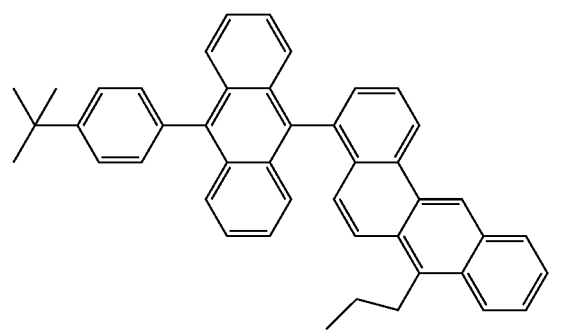
35
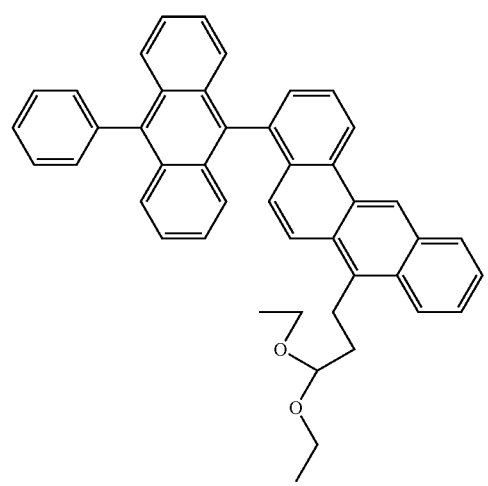
36
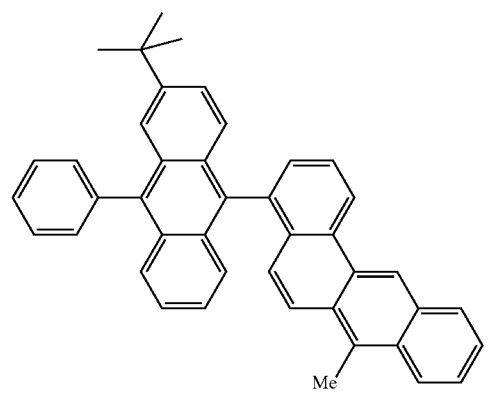
37
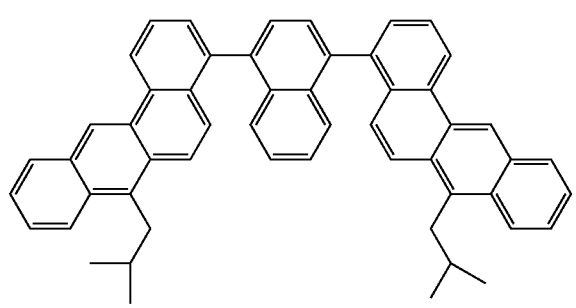

-continued
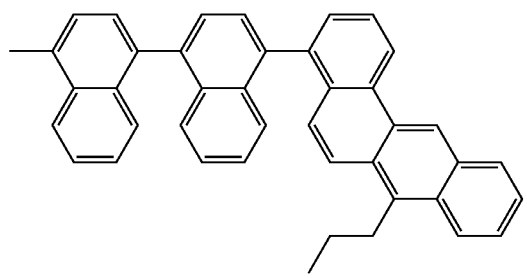
38
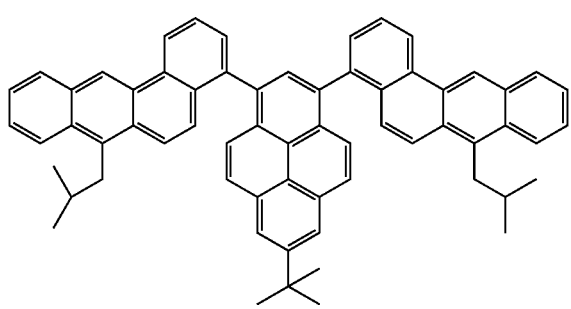
39
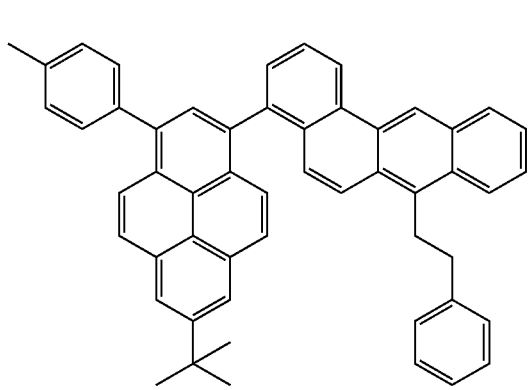
40
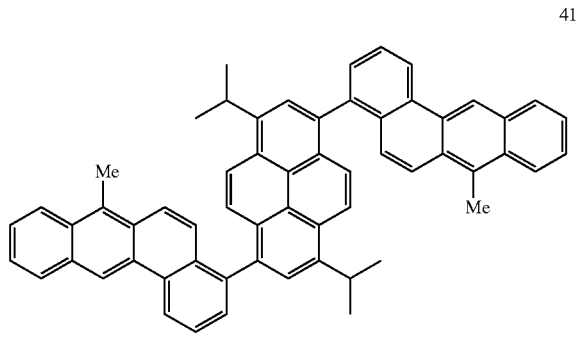
41
-continued
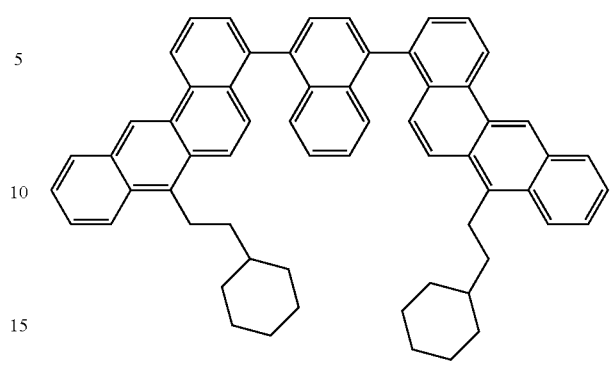
42
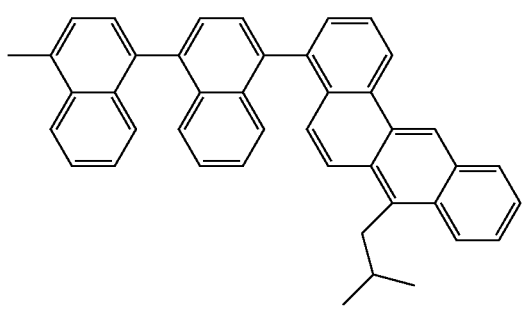
43
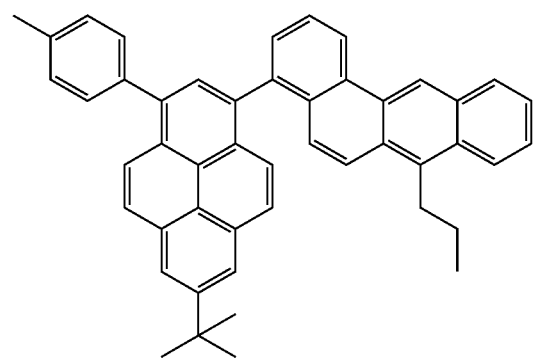
44
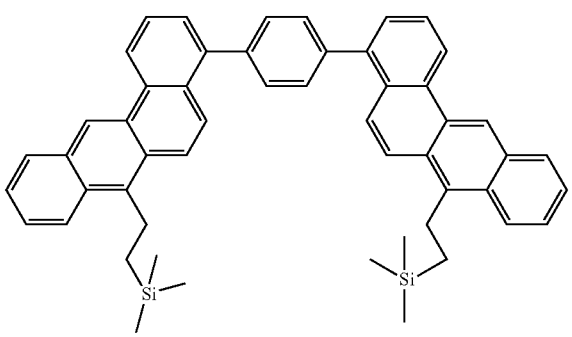
45

46
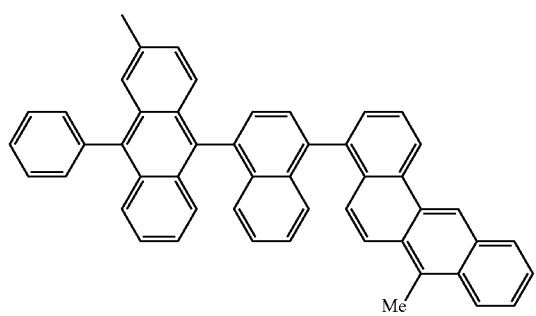
47
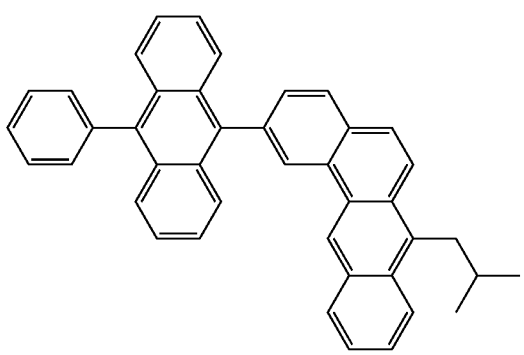
48
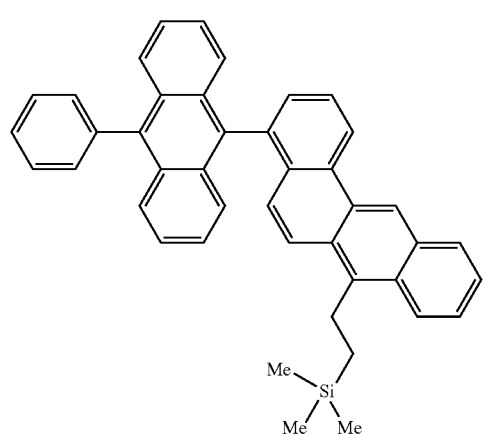
49
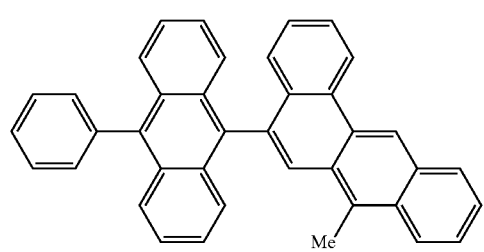
50
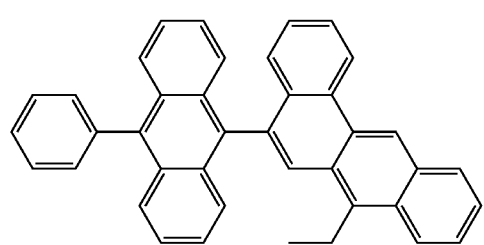
51
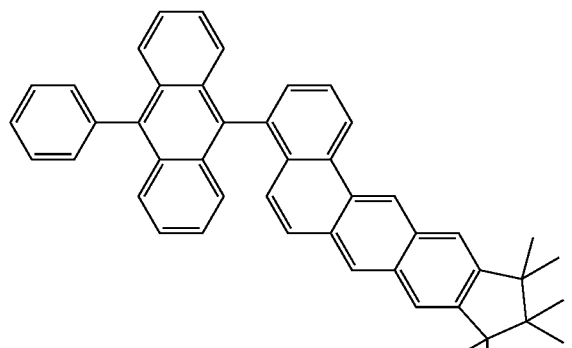
52
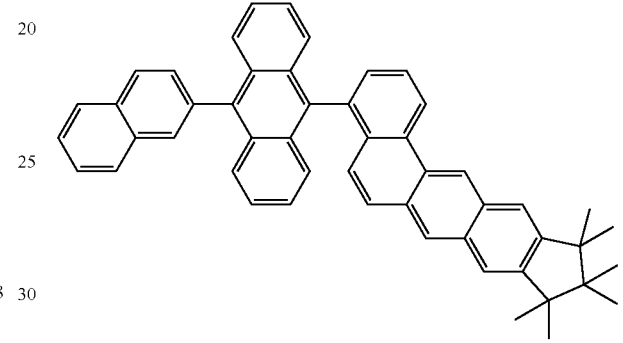
53
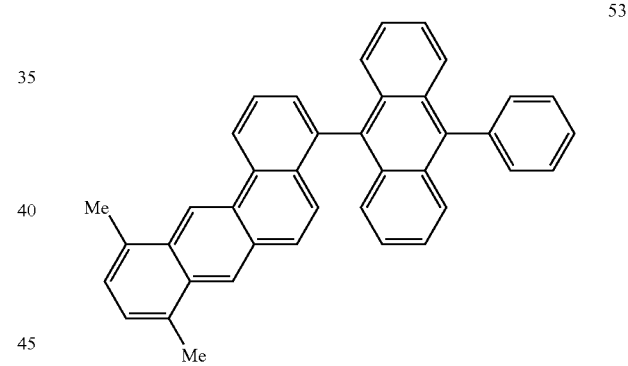
54
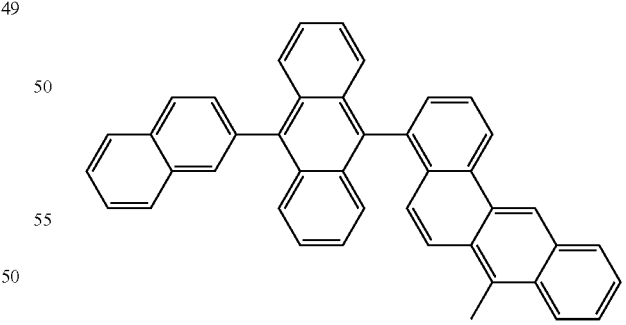
The compounds according to the invention can be prepared, for example, in accordance with the following reaction scheme (Scheme 1):

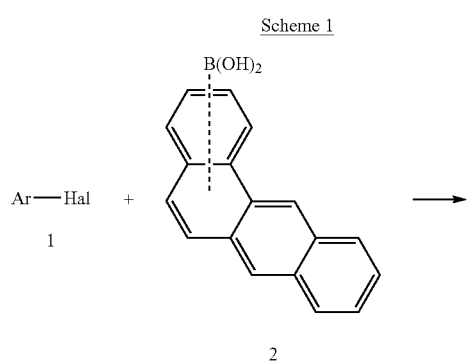

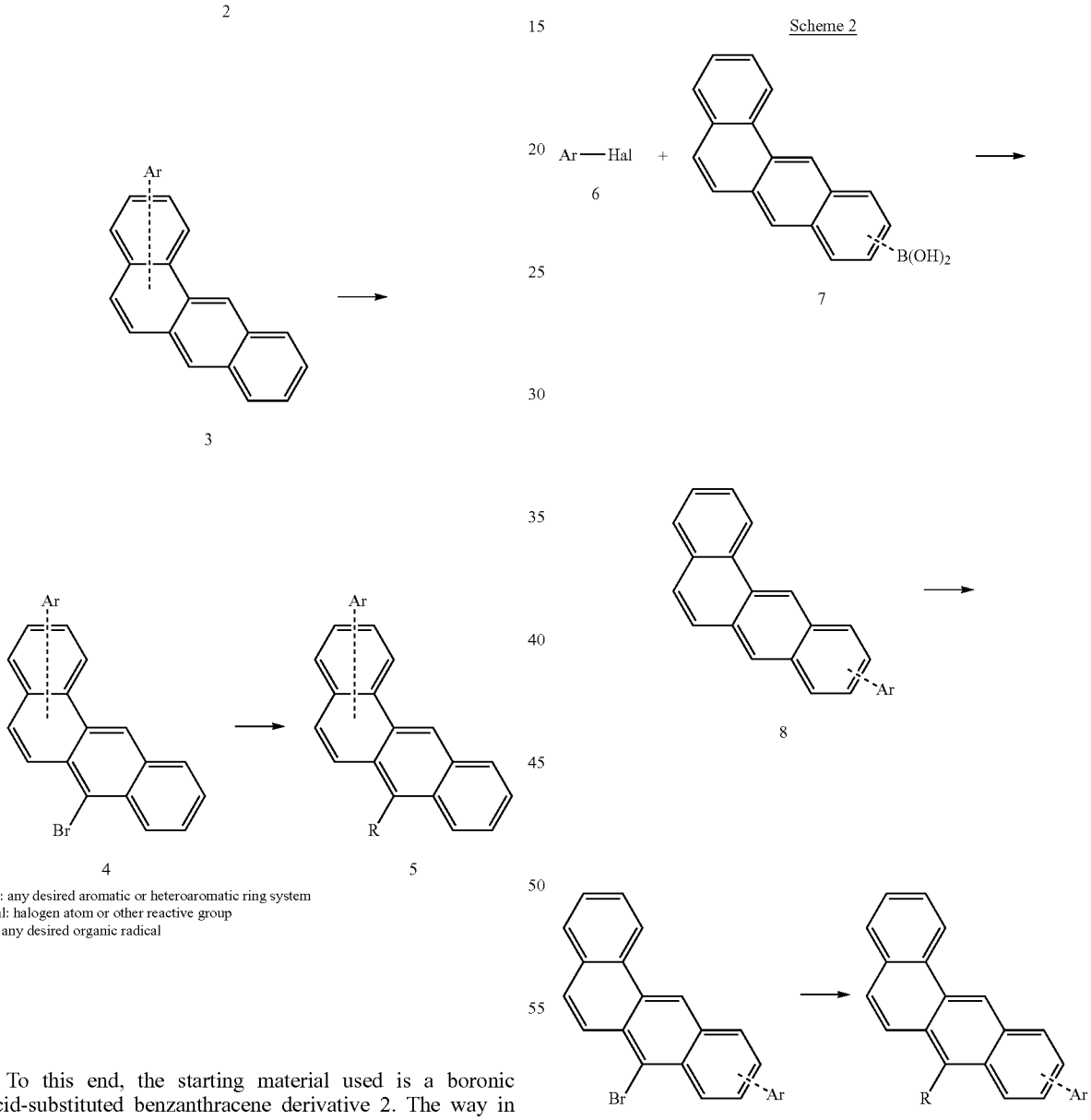

To this end, the starting material used is a boronic acid-substituted benzanthracene derivative 2. The way in which such compounds of the general structure 2 can be prepared is described in the working examples of WO 2008/145239. The boronic acid group here can be present in any desired position selected from positions 1-6 of the benzanthracene. A coupling reaction with any desired aromatic or heteroaromatic ring system which is substituted by a reactive group is subsequently carried out. This gives a compound of the general structure 3. This is subsequently brominated in the 7-position, and a radical R is introduced in the 7-position. The radical R is preferably an optionally substituted alkyl group.

An alternative synthesis scheme for obtaining the compounds according to the invention starts from benzanthracene derivatives which are substituted by aryl groups in the 8-, 9- or 11-position (Scheme 2). The way in which such compounds can be prepared is described, for example, in WO 2011/012212. This is followed, as described for Scheme 2, by bromination in the 7-position, and introduction of a group R, preferably an optionally substituted alkyl group.

Another alternative process for obtaining compounds according to the invention is shown in Scheme 3 below.

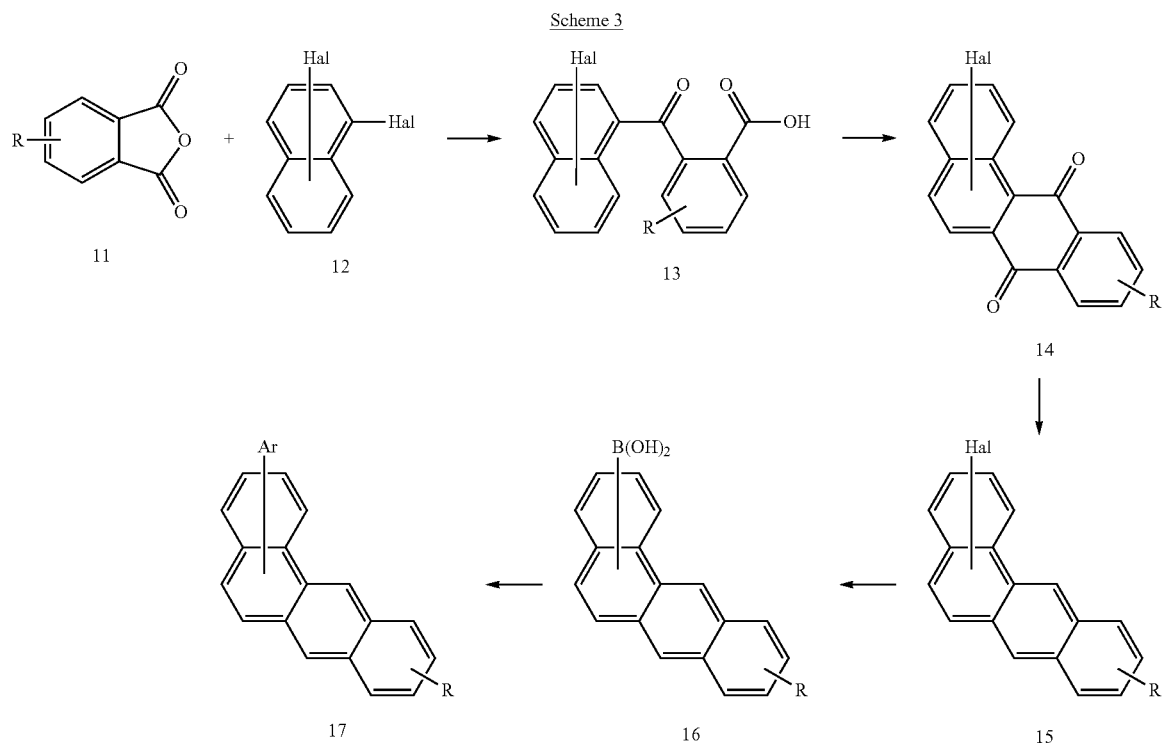

Scheme 3

Ar: any desired aromatic or heteroaromatic ring system
Hal: halogen atom or other reactive group
R: any desired organic radical To this end, firstly a phthalic anhydride derivative 11 is reacted with a substituted naphthyl compound 12. The compound 13 formed is reacted further in an intramolecular Friedel-Crafts acylation to give the quinone compound 14. This is reduced to a benzanthracene compound 15. A boronic acid function is subsequently introduced in the position of the reactive group Hal, giving a compound of the formula 16. A group Ar is subsequently introduced via a Suzuki reaction, giving the compound 17 according to the invention which contains a group R in one of positions 8-11 of the benzanthracene.

The application therefore relates to a process for the preparation of a compound of the formula (I) or (II) comprising steps 1) to 3) in the said sequence:

1) preparation of a benzanthracene compound which is substituted by one or more aromatic or heteroaromatic ring systems by a coupling reaction between a benzanthracene derivative and an aromatic or heteroaromatic ring system;
2) halogenation, preferably bromination, of the benzanthracene;
3) introduction of a substituent in the halogenated, preferably brominated, position.

In this process, the halogenation, preferably bromination, in step 2) preferably takes place in position 7 of the benzanthracene. It is furthermore preferred for the aromatic or heteroaromatic ring system Introduced by coupling reaction in step 1) to be present in a position selected from positions 1 to 6 on the benzanthracene.

The application furthermore relates to a process for the preparation of a compound of the formula (I) or (II) comprising the following steps in the sequence indicated:

I) preparation of a substituted benzanthracene derivative from a naphthyl derivative and a phthalic anhydride;
II) coupling reaction of the substituted benzanthracene derivative with an aromatic or heteroaromatic ring system.

Step I) preferably encompasses an acylation reaction, an intramolecular Friedel-Crafts acylation and a reduction of a quinone derivative. The substituent of the benzanthracene derivative is preferably present in a position of the benzanthracene selected from positions 8-11. The coupling reaction in step II) is preferably carried out at a position of the benzanthracene selected from positions 1-6, particularly preferably at a position selected from positions 4 and 5.

The compounds according to the invention described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I) or (II), where the bond(s) to the polymer, oligomer or dendrimer may be localised at any desired positions in formula (I) or (II) that are substituted by $R^1$, $R^2$ or $R^3$. Depending on the linking of the compound of the formula (I) or (II), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) or (II) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) or (II) may be linked via a trivalent or polyvalent group, for example via a trivalent or polyvalent aromatic or heteroaromatic group, to form a branched or dendritic oligomer or polymer.

The same preferences as described above for compounds of the formula (I) or (II) apply to the recurring units of the formula (I) or (II) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers and oligomers according to the invention are generally prepared by polymerisation of one or more types of monomer, at least one monomer of which results in recurring units of the formula (I) or (II) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or (II) or at least one polymer, oligomer or dendrimer containing at least one unit of the formula (I) or (II), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (OLEDs). Depending on the substitution, the compounds are employed in different functions and layers.

The compounds according to the invention can be employed in any function in the organic electroluminescent device, for example as matrix material, as emitting material, as hole-transporting material or as electron-transporting material. Preference is given to the use as matrix material in an emitting layer, preferably a fluorescent emitting layer, and the use as emitting material, preferably as fluorescent emitting material, in an emitting layer of an organic electroluminescent device.

The invention therefore furthermore relates to the use of a compound of the formula (I) or (II) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (I) or (II). The electronic device here is preferably selected from the devices indicated above. Particular preference is given to an organic electroluminescent device comprising anode, cathode and at least one emitting layer, characterised in that at least one organic layer comprises at least one organic compound of the formula (I) or (II). Very particular preference is given to an organic electroluminescent device comprising anode, cathode and at least one emitting layer comprising at least one organic compound of the formula (I) or (II).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device is preferably the following:
anode-hole-injection layer-hole-transport layer-emitting layer-electron-transport layer-electron-injection layer-cathode. It is not necessary for all of the said layers to be resent here, and in addition further layers may be present, for example an electron-blocking layer adjacent to the emitting layer on the anode side, or a hole-blocking layer adjacent to the emitting layer on the cathode side.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) or (II) and where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour. The compounds according to the invention may alternatively and/or additionally also be present in the hole-transport layer or in another layer in an organic electroluminescent device of this type.

The compound according to the invention is particularly suitable for use as matrix compound for an emitter compound, preferably a blue-emitting emitter compound, or as emitter compound, preferably as blue-emitting emitter compound.

Preference is given to the use as matrix compound for fluorescent emitter compounds.

However, the compound according to the invention can also be used as matrix compound for emitter compounds which exhibit thermally activated delayed fluorescence (TADF). The basic principles of the emission mechanism in TADF are disclosed in H. Uoyama et al., Nature 2012, 492, 234.

If the compound according to the invention is employed as matrix material, it can be employed combined with any desired emitting compounds known to the person skilled in the art. It is preferably employed in combination with the preferred emitting compounds indicated below, particularly the preferred fluorescent compounds indicated below.

In the case where the emitting layer of the organic electroluminescent device comprises a mixture of an emitting compound and a matrix compound, the following applies:

The proportion of the emitting compound in the mixture of the emitting layer is preferably between 0.1 and 50.0%, particularly preferably between 0.5 and 20.0%, and very particularly preferably between 1.0 and 10.0%. Correspondingly, the proportion of the matrix material or matrix materials is preferably between 50.0 and 99.9%, particularly preferably between 80.0 and 99.5%, and very particularly preferably between 90.0 and 99.0%.

The indications of the proportions in % in the context of the present application are taken to mean % by vol. if the compounds are applied from the gas phase, and they are taken to mean % by weight if the compounds are applied from solution.

If the compound according to the invention is employed as emitting compound in an emitting layer, it is preferably employed in combination with one or more matrix materials. The preferred proportions of emitting compound and matrix material here are as indicated above.

The compound according to the invention can furthermore also be employed as electron-transporting compound in an electron-transport layer, a hole-blocking layer or an electron-injection layer. For this purpose, it is preferred for the compound according to the invention to contain one or more substituents selected from electron-deficient heteroaryl groups, such as, for example, triazine, pyrimidine or benzimidazole.

Generally preferred classes of material for use as corresponding functional materials in the organic electroluminescent devices according to the invention are indicated below.

Suitable phosphorescent emitting compounds are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitting compounds used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent emitting compounds described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able, without inventive step, to employ further phosphorescent complexes in combination with the compounds according to the invention in OLEDs.

Preferred fluorescent emitters, besides the compounds according to the invention, are selected from the class of the arylamines. An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and WO 2013/185871. Preference is likewise given to the benzoindenofluorenamines disclosed in WO 2014/037077, the benzofluorene-amines disclosed in WO 2014/106522 and the extended indenofluorenes disclosed in WO 2014/111269.

Preferred fluorescent emitting compounds are depicted in the following table:

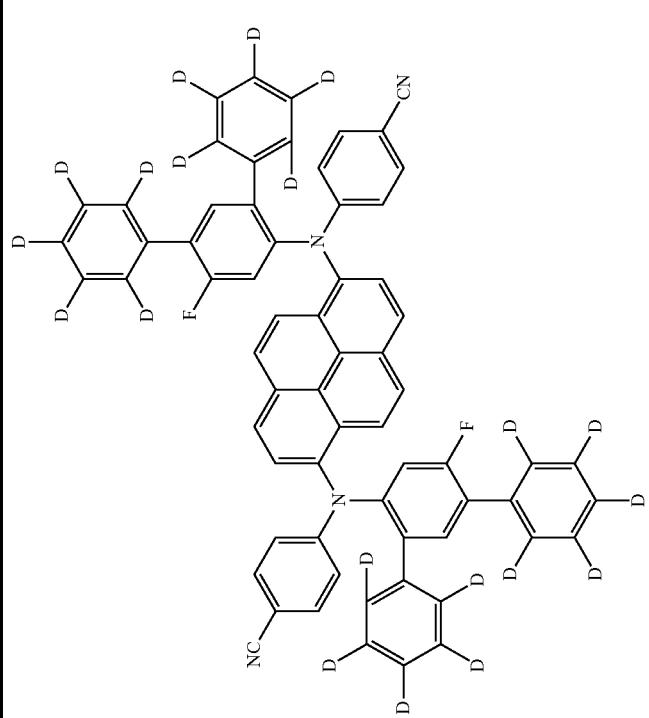
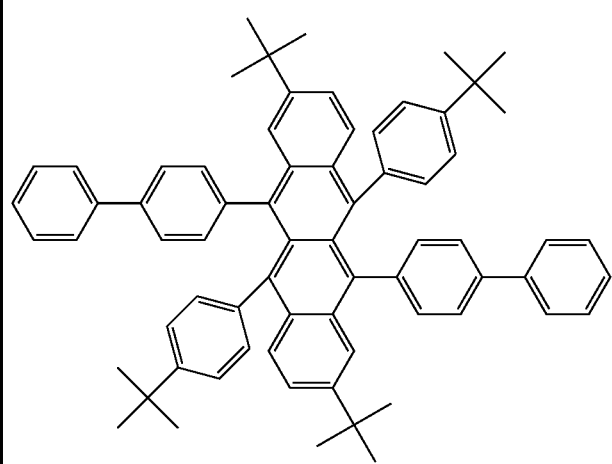

-continued
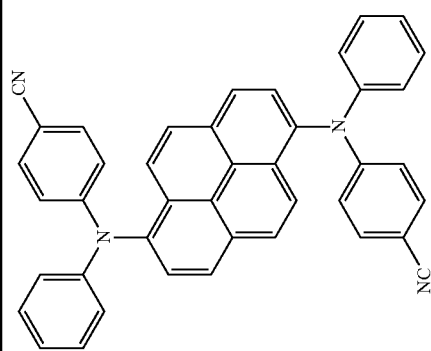 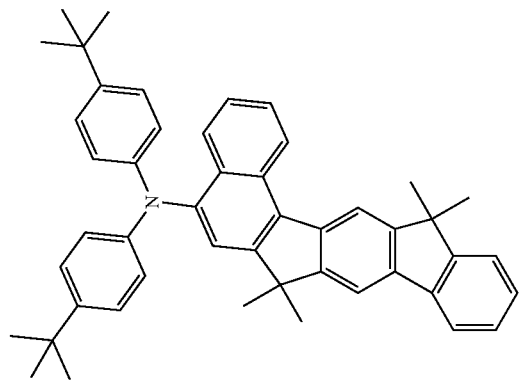
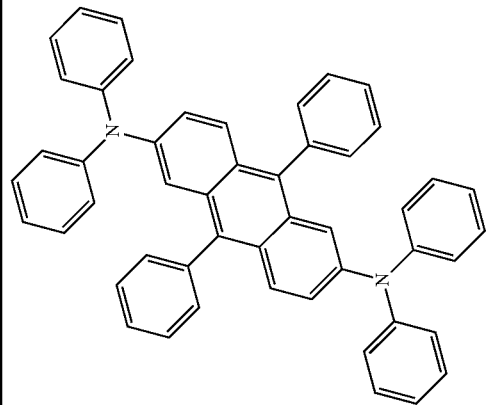 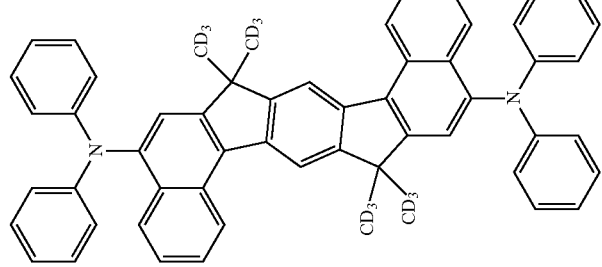

-continued
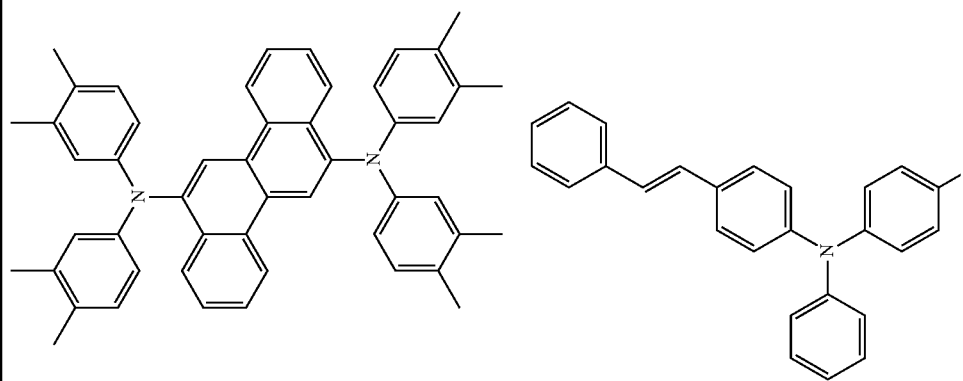
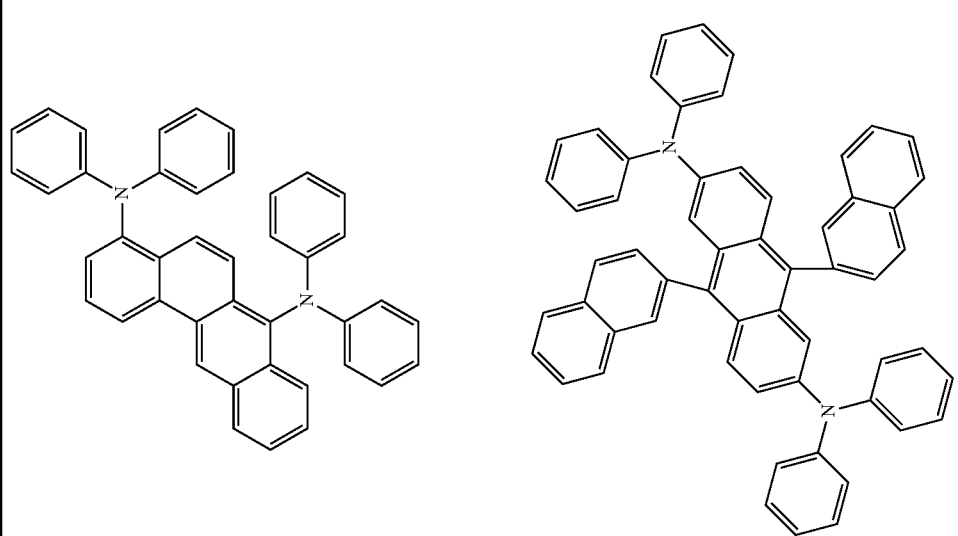

-continued
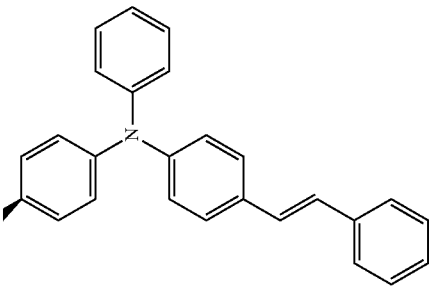
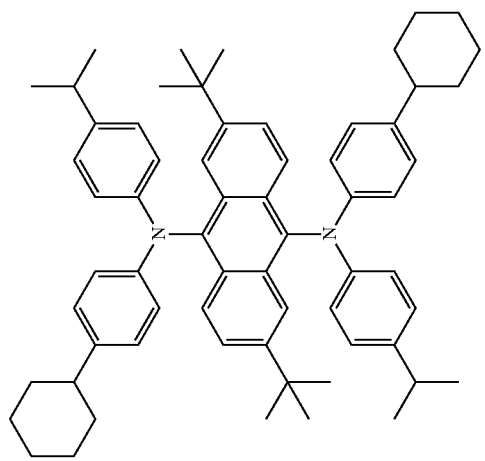
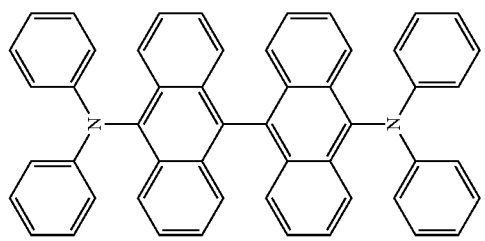

-continued
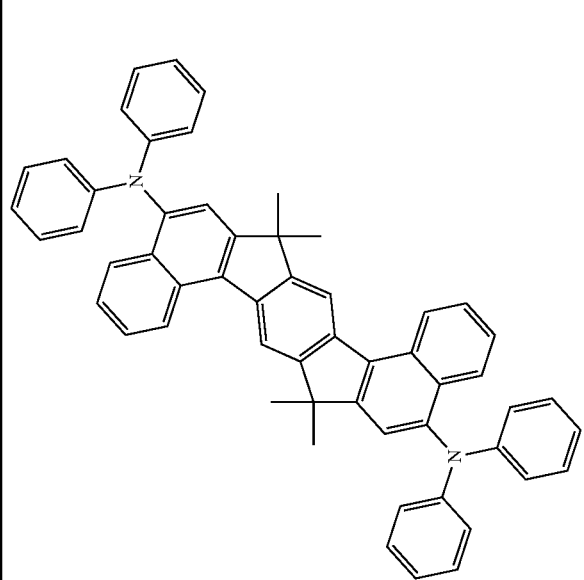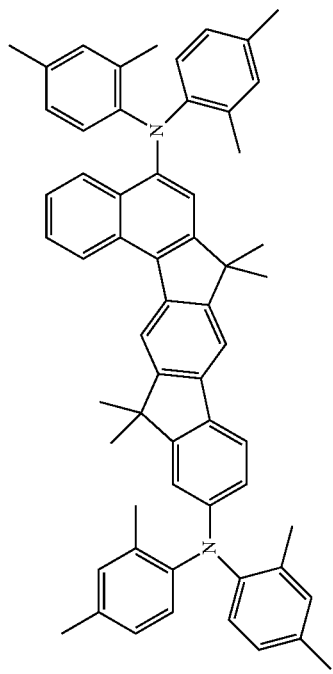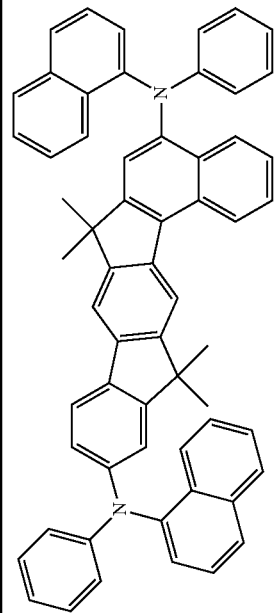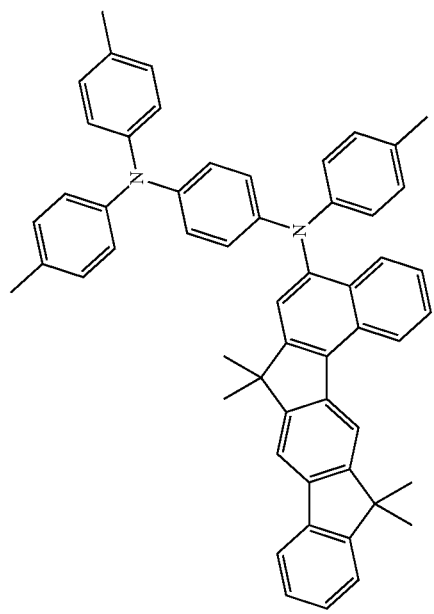

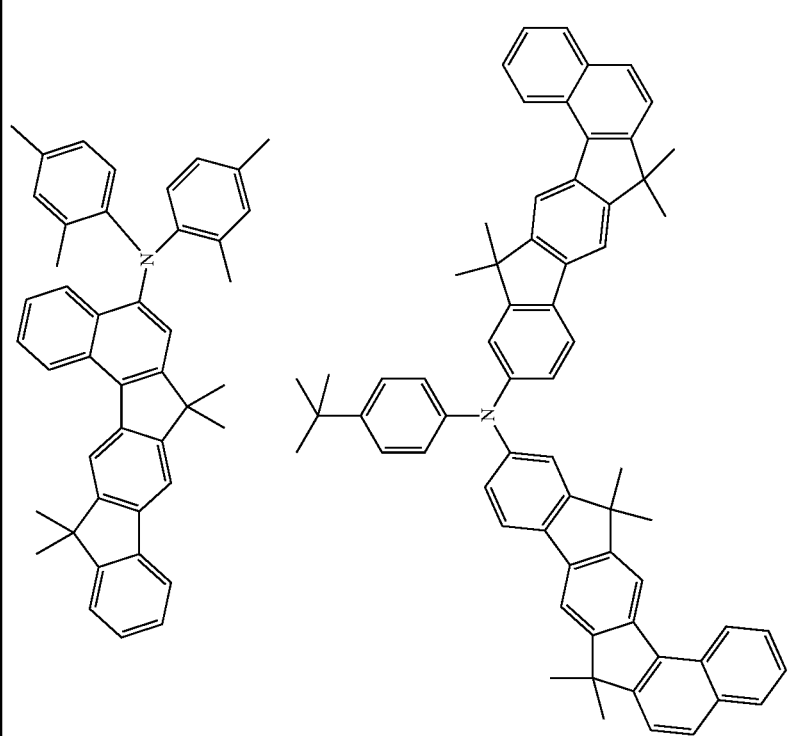
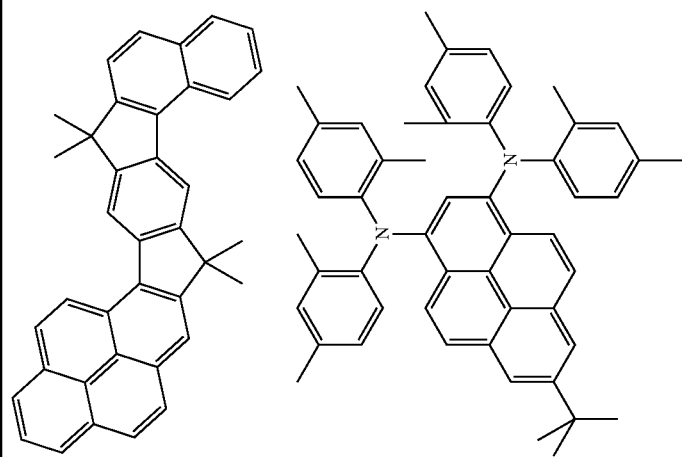

-continued
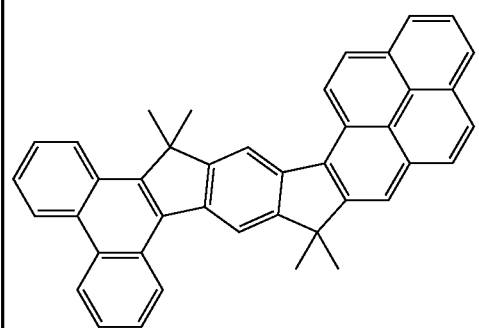
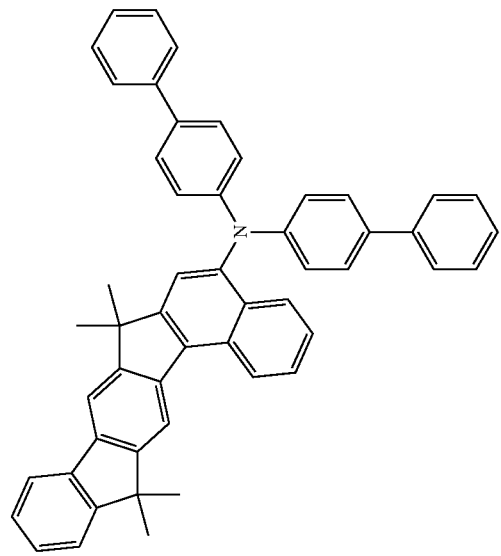
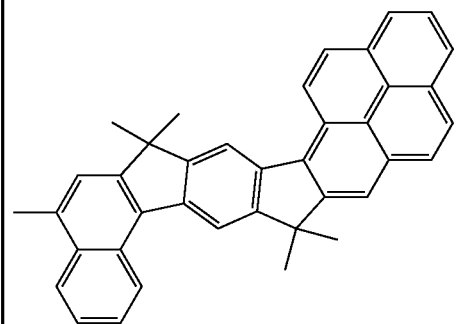
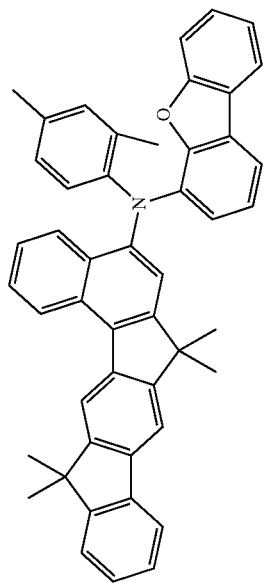

-continued
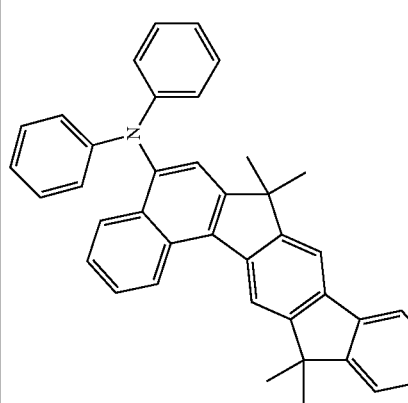
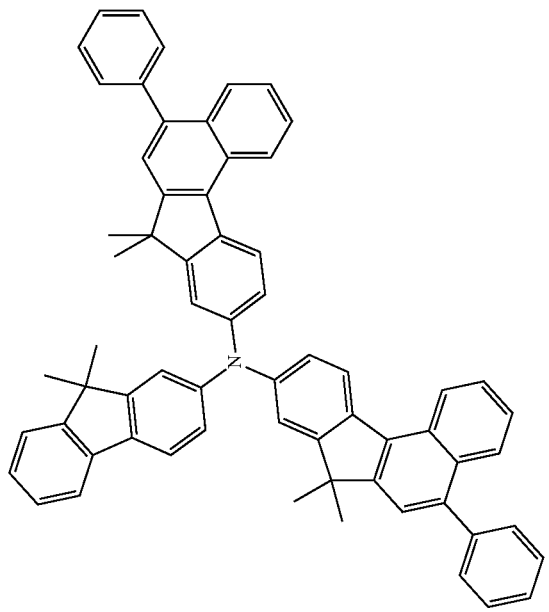
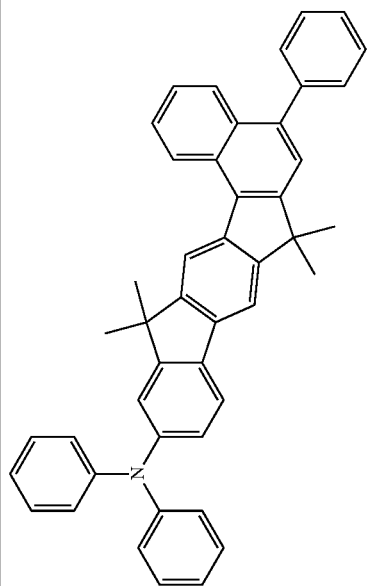
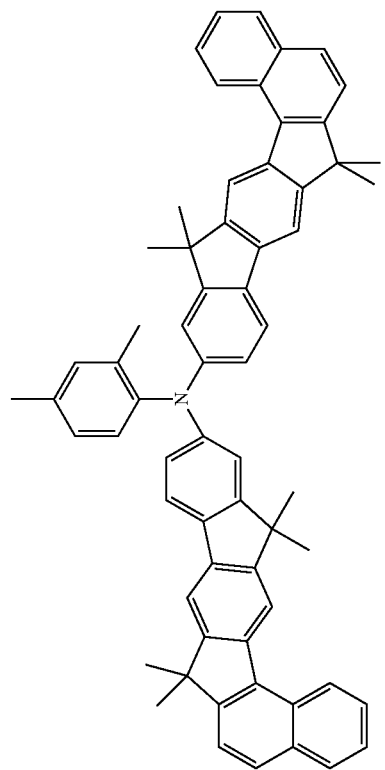

-continued
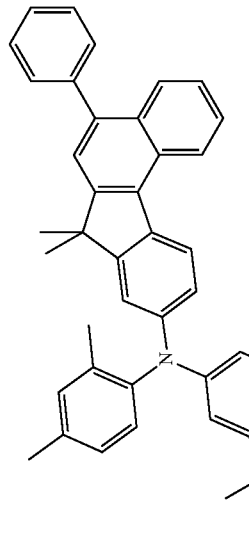 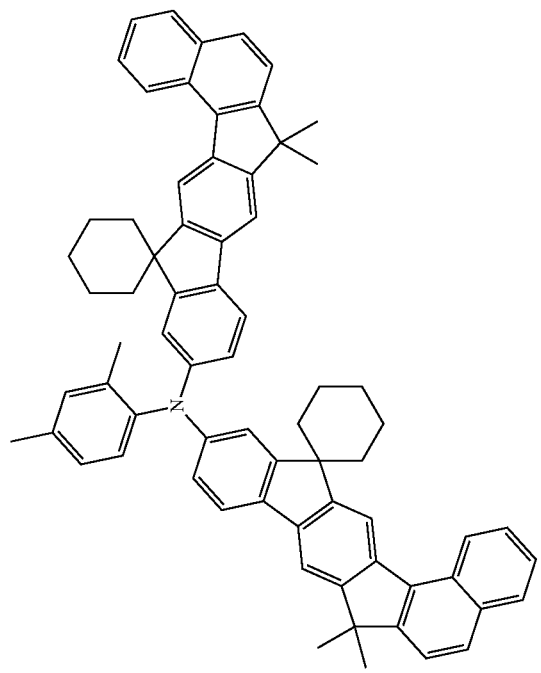
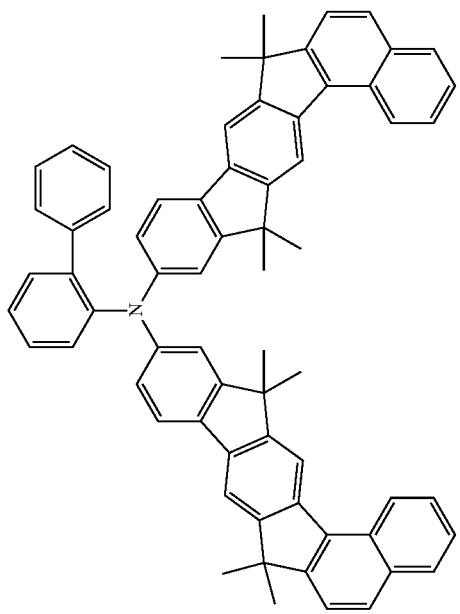 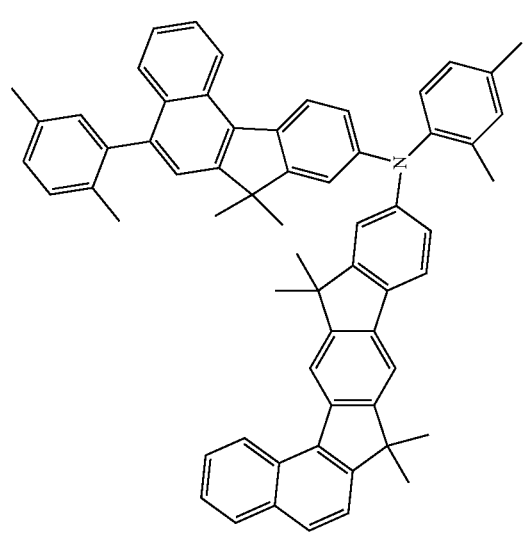

-continued
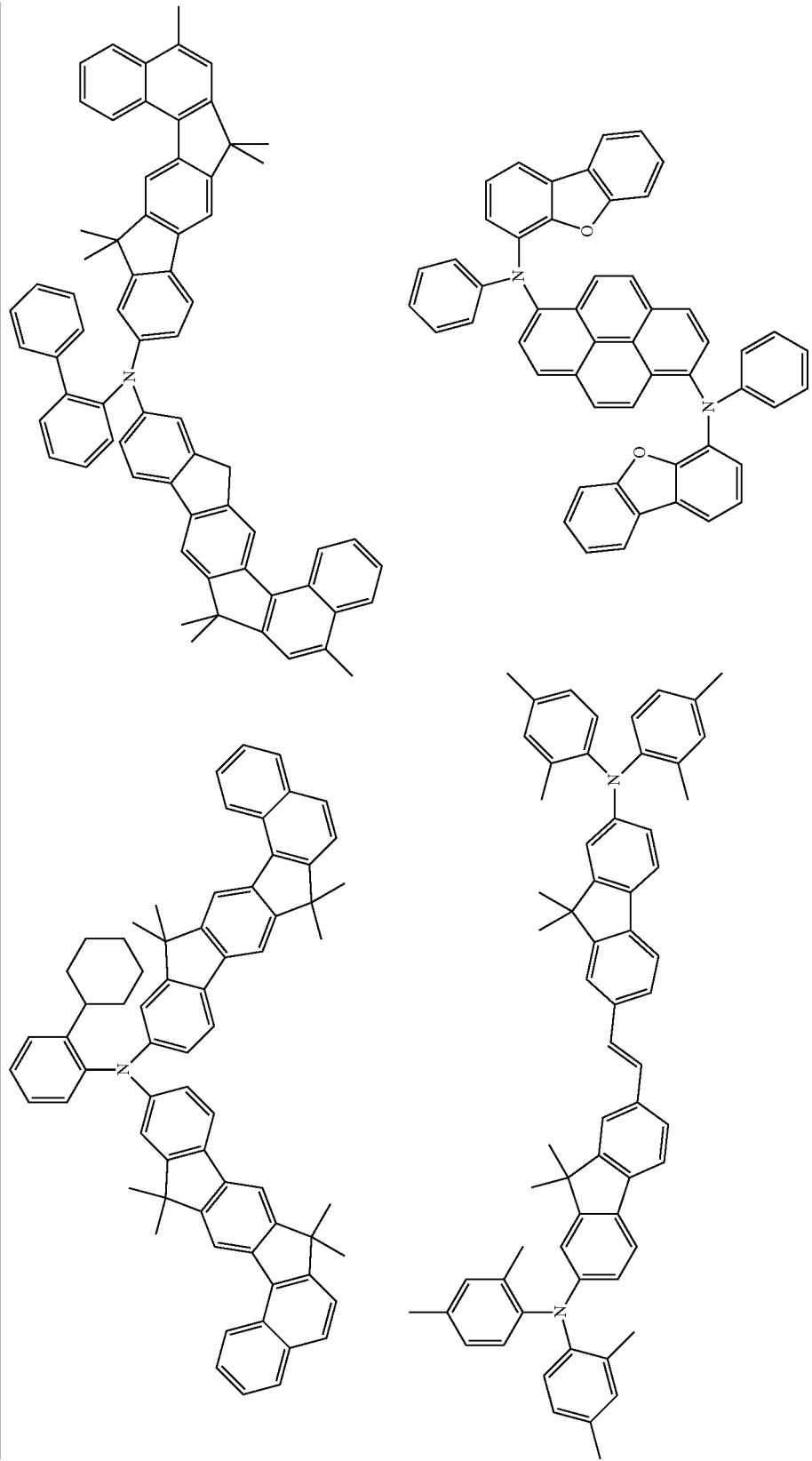

-continued
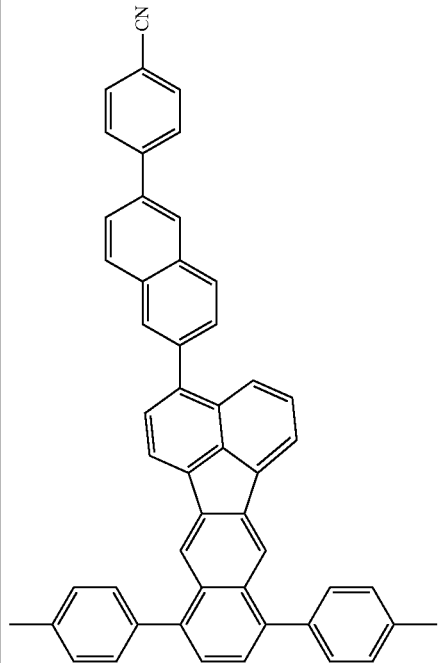
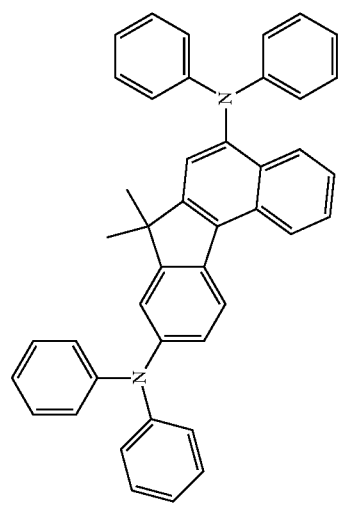
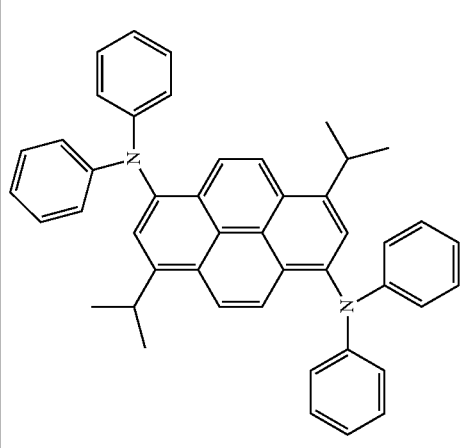
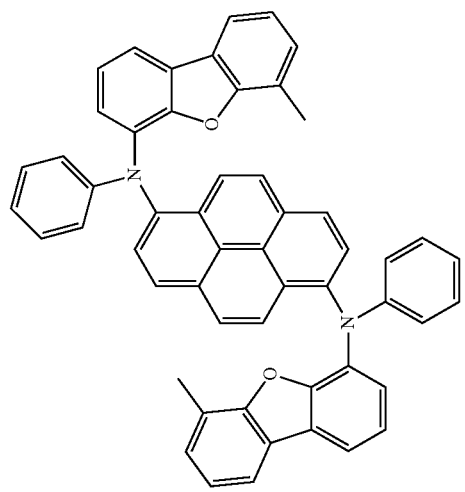

-continued
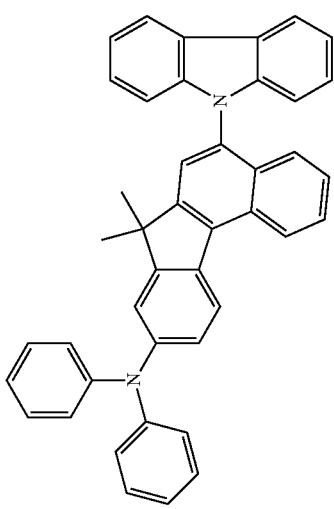

Preferred matrix materials for phosphorescent emitting compounds are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, and diazaphosphole derivatives, for example in accordance with WO 2010/054730.

Preferred matrix materials for use in combination with fluorescent emitting compounds, besides the compounds of the formula (I) or (II), are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Examples of preferred hole-transport materials which can be used in a hole-transport, hole-injection or electron-blocking layer in the electroluminescent device according to the invention, besides the compounds of the formula (I) or (II), are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with WO 2014/015937, WO 2014/015938 and WO 2014/015935), spirodibenzopyranamines (for example in accordance with WO 2013/083216) and dihydroacridine derivatives (for example in accordance with WO 2012/150001).

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing.

For the production of an organic electroluminescent device according to the invention, it is furthermore preferred to apply one or more layers from solution and one or more layers by a sublimation process.

Owing to the good solubility of the compounds of the formula (I) or (II), it is preferred for the layer comprising one or more compounds of the formula (I) or (II) to be applied from solution. This is preferably the emitting layer of an organic electroluminescent device.

In accordance with the invention, the electronic devices comprising one or more compounds according to the invention can be employed in displays, as light sources in lighting applications and as light sources in medical and/or cosmetic applications (for example light therapy).

WORKING EXAMPLES

A) Synthesis Examples

The compounds according to the invention are prepared in accordance with the following synthesis scheme:

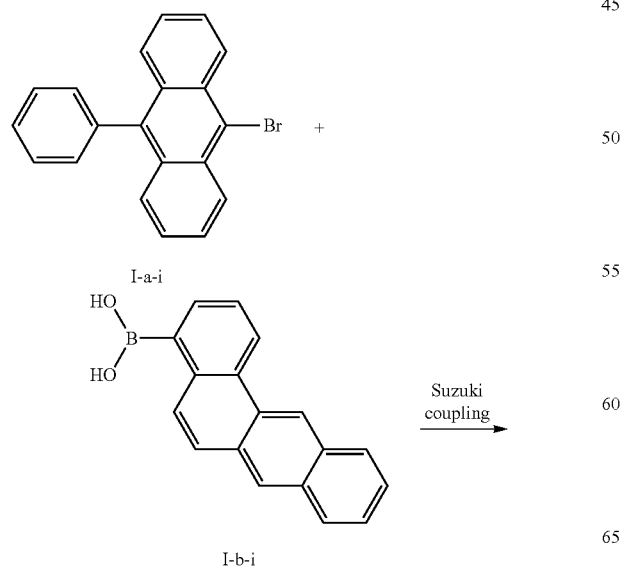

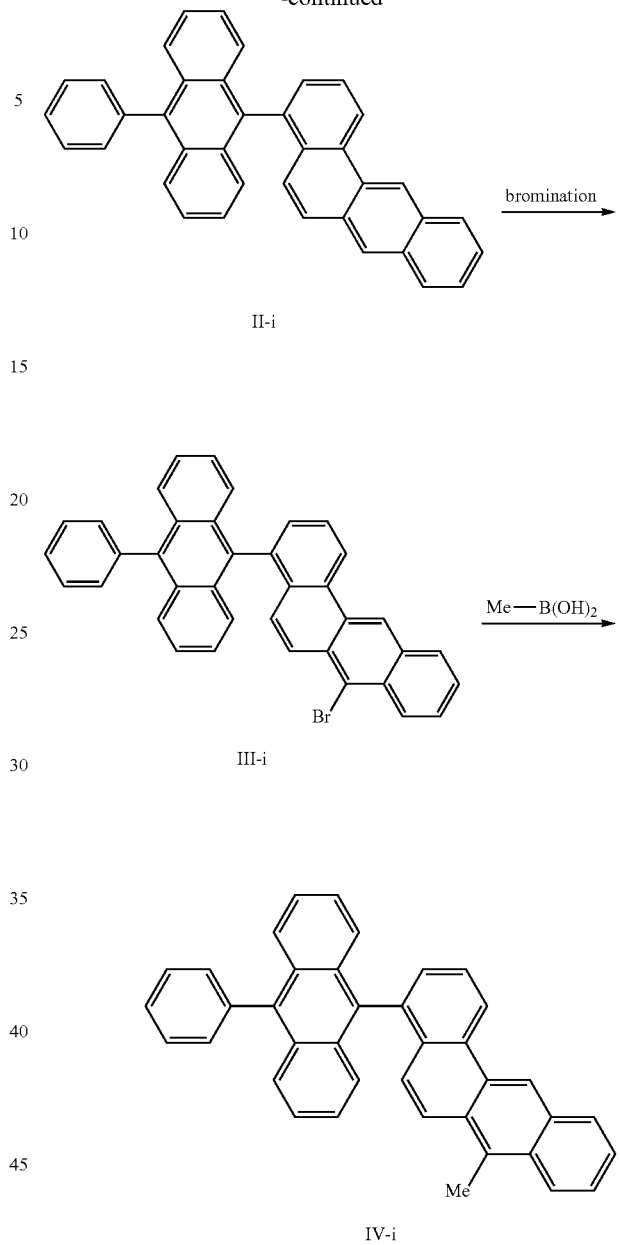

To this end, firstly a benzanthracene-aryl compound II is prepared via a Suzuki coupling between a benzanthracene-boronic acid derivative I-b and an aryl bromide I-a (step 1). The compound is subsequently brominated to give a bromobenzanthracene compound III (step 2). In a final step 3, a substituent is introduced at the position of the bromine via a Suzuki coupling, giving the compound IV according to the invention.

Step 1

4-(10-Phenylanthracen-9-yl)benzo[a]anthracene II-i is synthesised in accordance with the following literature procedure: WO 2008/145239, Working Example 8.

The following compounds are prepared analogously:

| Starting material I-a | Starting material I-b | Product II | Yield |
|---|---|---|---|
| 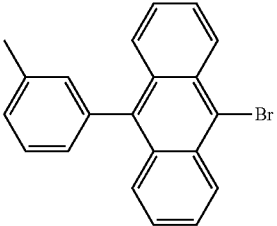 [SMILES: Cc1cccc(-c2c3ccccc3c(Br)c3ccccc23)c1] | 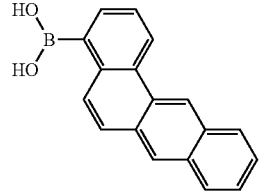 [SMILES: OB(O)c1cccc2c1ccc1cc3ccccc3cc12] | 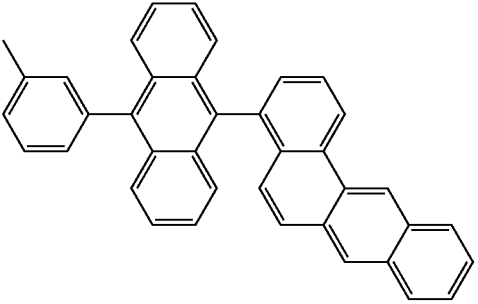 [SMILES: Cc1cccc(-c2c3ccccc3c(-c3cccc4c3ccc3cc5ccccc5cc34)c3ccccc23)c1] | 67% |
| 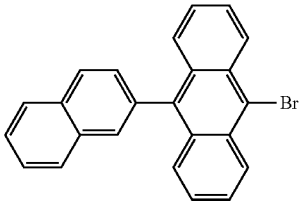 [SMILES: Brc1c2ccccc2c(-c2ccc3ccccc3c2)c2ccccc12] | 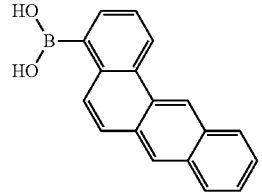 [SMILES: OB(O)c1cccc2c1ccc1cc3ccccc3cc12] | 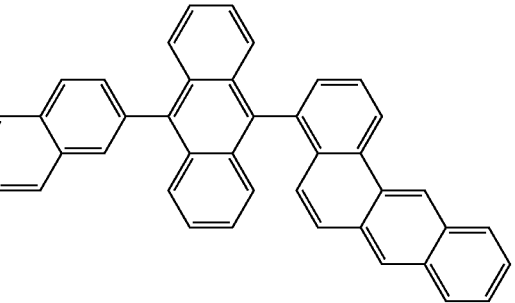 | 59% |
| 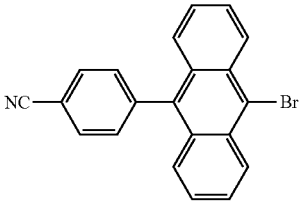 [SMILES: N#Cc1ccc(-c2c3ccccc3c(Br)c3ccccc23)cc1] | 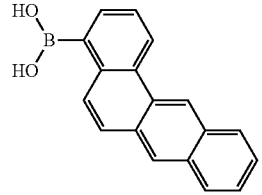 [SMILES: OB(O)c1cccc2c1ccc1cc3ccccc3cc12] | 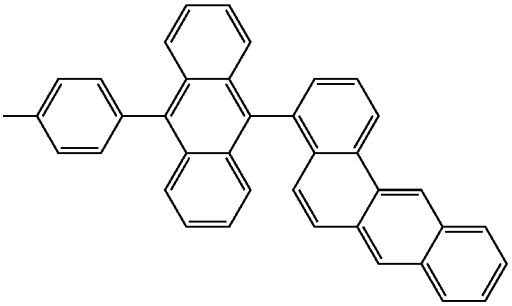 | 52% |
| 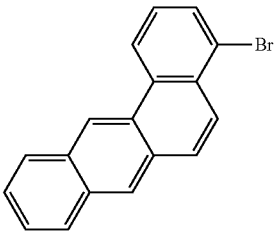 [SMILES: Brc1cccc2c1ccc1cc3ccccc3cc12] | 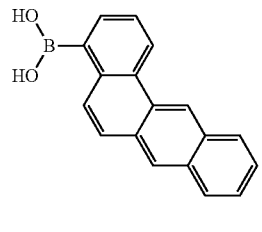 [SMILES: OB(O)c1cccc2c1ccc1cc3ccccc3cc12] | 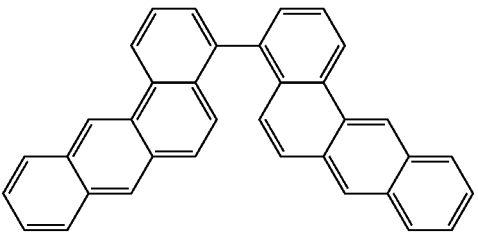 [SMILES: c1ccc2cc3c(ccc4c(-c5cccc6c5ccc5cc7ccccc7cc56)cccc43)cc2c1] | 72% |

Step 2

7-Bromo-4-(10-phenylanthracen-9-yl)benzo[a]anthracene III-i 1 l of tetrahydrofuran is added to 4-(10-phenylanthracen-9-yl)benzo[a]-anthracene II-i (50 g, 104.0 mmol), N-bromosuccinimide (24.02 g, 135 mmol) and benzoyl peroxide (containing 25% of water) (12.7 ml, 20.8 mmol). The batch is heated under reflux overnight, cooled to room temperature and extended with 800 ml of chloroform and 500 ml of a 10% sodium thiosulfate solution. After phase separation, the aqueous phase is extracted a number of times with chloroform. The combined organic phases are washed with dist. water, dried over magnesium sulfate and filtered through aluminium oxide. The organic phase is evaporated. The residue is brought to precipitation using chlorobenzene and recrystallised from heptane, giving compound III-i as pale-yellow solid: 58.2 g (87% of theory).

As an alternative, NBS/HBr or bromine (catalytic) can be utilised as bromine source. In order to avoid overbromination, reactions were carried out at low temperature (for example −10° C.).

The following compounds are prepared analogously:

| Starting material II | Product III | Yield |
|---|---|---|
| | | 53% |
| | | 64% |
| | | 68% |
| | | 64% |

Step 3

7-Methyl-4-(10-phenylanthracen-9-yl)benzo[a]anthracene IV-i 5.47 g (97%, 88.6 mmol) of methylboronic acid, 25 g (44.3 mmol) of 7-bromo-4-(10-phenylanthracen-9-yl)benzo[a]anthracene III-i and 20.4 g (88.6 mmol) of $K_3PO_4 \cdot H_2O$ are suspended in 500 ml of toluene. 1.09 g (2.66 mmol) of dicyclohexyl(2',6'-dimethoxybiphenyl-2-yl)phosphine (SPhos) and 0.3 g (1.33 mmol) of palladium acetate are added to this suspension, and the reaction mixture is heated under reflux for 16 h. After cooling, the reaction mixture is diluted with water, the organic phase is separated off, washed three times with 100 ml of water and subsequently evaporated to dryness. After filtration of the crude product through silica gel with toluene, the residue remaining is recrystallised from toluene/heptane. The yield is 17.3 g (79% of theory).

The following compounds IV according to the invention are prepared analogously:

| No. | Starting material III | Boronic acid or boronic acid ester | Product IV | Yield |
|---|---|---|---|---|
| 1 | | | | 64% |
| 2 | | | | 76% |
| 3 | | | | 69% |
| 4 | | | | 58% |
| 5 | | | | 47% |

-continued

| No. | Starting material III | Boronic acid or boronic acid ester | Product IV | Yield |
|---|---|---|---|---|
| 6 | | HO-B(OH)-CH2-CH2-Ph | | 65% |
| 7 | | Me—B(OH)₂ | | 59% |
| 8 | | HO-B(OH)-CH2-CH(CH3)2 | | 62% |
| 9 | | HO-B(OH)-CH2-CH2-Ph | | 72% |
| 10 | | HO-B(OH)-CH2-CH3 | | 74% |

-continued

| No. | Starting material III | Boronic acid or boronic acid ester | Product IV | Yield |
|-----|----------------------|-----------------------------------|------------|-------|
| 11  |                      | Me—B(OH)₂                         |            | 52%   |
| 12  |                      |                                   |            | 38%   |
| 13  |                      |                                   |            | 47%   |
| 14  |                      |                                   |            | 43%   |
| 15  |                      |                                   |            | 76%   |

| No. | Starting material III | Boronic acid or boronic acid ester | Product IV | Yield |
|---|---|---|---|---|
| 16 | | | | 68% |
| 17 | | | | 73% |

B) Device Examples

B-1) Device Examples from the Gas Phase: Production of OLEDs

OLEDs according to the invention and OLEDs in accordance with the prior art are produced by a general process in accordance with WO 04/058911, which is adapted to the circumstances described here (layer-thickness variation, materials).

The substrates used are glass substrates coated with structured ITO (indium tin oxide) in a thickness of 50 nm. A layer of Clevios P VP AI 4083 (purchased from Heraeus Clevios GmbH, Leverkusen) with a thickness of 20 nm is applied by spin coating as buffer layer. All remaining materials are applied by thermal vapour deposition in a vacuum chamber.

The structure A used is as follows:
substrate,
ITO (50 nm),
buffer layer (20 nm),
hole-Injection layer (HTL1 95%, HIL 5%) (20 nm),
hole-transport layer (HTL1) (20 nm),
emission layer (95% of host, 5% of dopant) (20 nm),
electron-transport layer (50% of ETL+50% of EIL) (30 nm),
electron-injection layer (EIL) (3 nm),
cathode (Al) (100 nm).

The materials used are shown in Table 1.
The emission layer (EML) always consists of at least one matrix material (host=H) and an emitting dopant (dopant=D), which is admixed with the matrix material in a certain proportion by volume by co-evaporation. An expression such as H-1:D1 (95%:5%) here means that material H-1 is present in the layer in a proportion by volume of 95% and D1 is present in the layer in a proportion of 5%.

The OLEDs are characterised by standard methods. For this purpose, the electroluminescence spectra are recorded, the current efficiency (measured in cd/A) and the external quantum efficiency (EQE, measured in percent) as a function of the luminous density assuming Lambert emission characteristics are calculated from current/voltage/luminous density characteristic lines (IUL characteristic lines), and finally the lifetime of the components is determined. The electroluminescence spectra are recorded at a luminous density of 1000 cd/m$^2$, and the CIE 1931 x and y colour coordinates are calculated therefrom. The term EQE @ 1000 cd/m$^2$ denotes the external quantum efficiency at an operating luminous density of 1000 cd/m$^2$. The lifetime LT95 @ 1000 cd/m$^2$ is the time which passes until the initial luminance has dropped by 5% from 1000 cd/m$^2$. The data obtained for the various OLEDs are summarised in Table 2.

The compounds according to the invention are particularly suitable as matrix materials in blue-fluorescent OLEDs (see Examples V1-V5 and E6-E11). Two standard matrix materials VH-1 and VH-2, each comprising one of the dopants D1, D2 and D3 which fluoresce in the dark blue, serve as comparison. Matrices H-1 and H-2 are shown as compounds according to the invention. These are likewise used in combination with one of the dopants D1, D2 and D3.

TABLE 1
Structures of the materials used
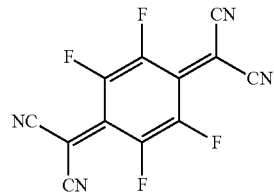 [SMILES: N#CC(C#N)=c1c(F)c(F)c(=C(C#N)C#N)c(F)c1F]
HIL
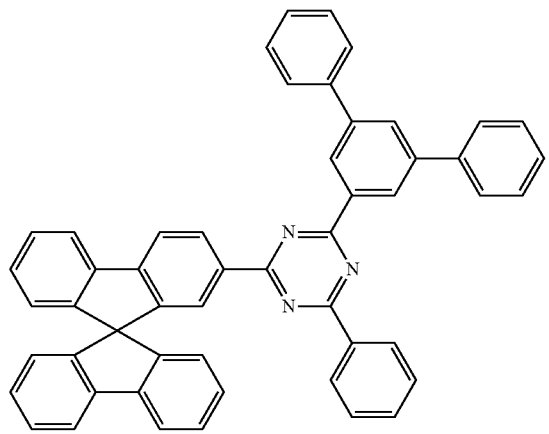 [SMILES: c1ccc(-c2cc(-c3ccccc3)cc(-c3nc(-c4ccccc4)nc(-c4ccc5c(c4)C4(c6ccccc6-c6ccccc64)c4ccccc4-5)n3)c2)cc1]
ETL
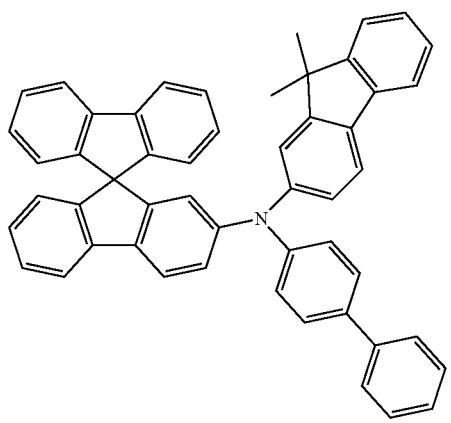 [SMILES: CC1(C)c2ccccc2-c2ccc(N(c3ccc(-c4ccccc4)cc3)c3ccc4c(c3)C3(c5ccccc5-c5ccccc53)c3ccccc3-4)cc21]
HTL1
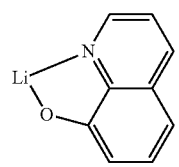
EIL
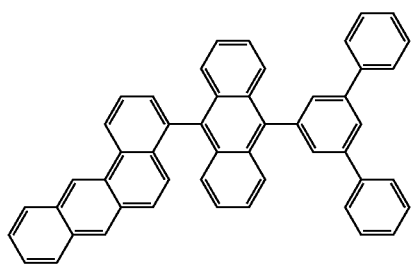 [SMILES: c1ccc(-c2cc(-c3ccccc3)cc(-c3c4ccccc4c(-c4cccc5c4ccc4cc6ccccc6cc45)c4ccccc34)c2)cc1]
VH-1
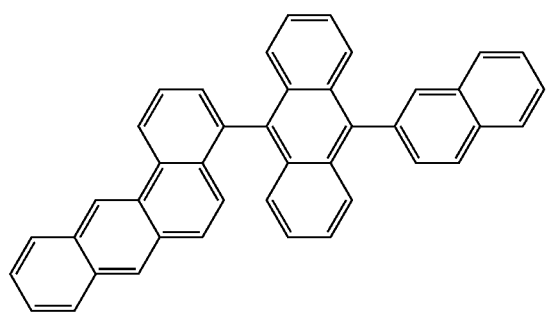 [SMILES: c1ccc2cc(-c3c4ccccc4c(-c4cccc5c4ccc4cc6ccccc6cc45)c4ccccc34)ccc2c1]
VH-2

TABLE 1-continued
Structures of the materials used
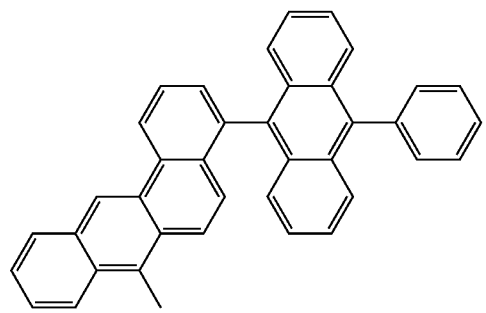 [SMILES: Cc1c2ccccc2cc2c1ccc1c(-c3c4ccccc4c(-c4ccccc4)c4ccccc34)cccc12]
H-1
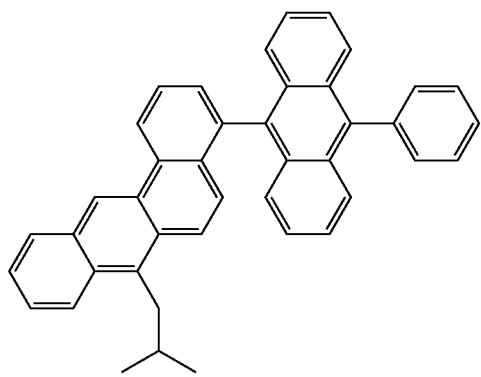 [SMILES: CC(C)Cc1c2ccccc2cc2c1ccc1c(-c3c4ccccc4c(-c4ccccc4)c4ccccc34)cccc12]
H-2
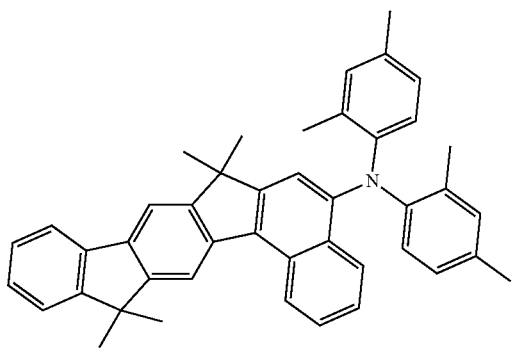 [SMILES: Cc1ccc(N(c2ccc(C)cc2C)c2cc3c(c4ccccc24)-c2cc4c(cc2C3(C)C)-c2ccccc2C4(C)C)c(C)c1]
D1
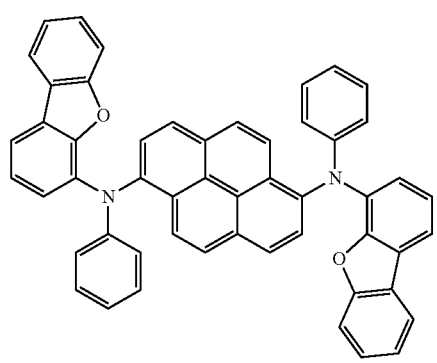 [SMILES: c1ccc(N(c2ccc3ccc4c(N(c5ccccc5)c5cccc6c5oc5ccccc56)ccc5ccc2c3c54)c2cccc3c2oc2ccccc23)cc1]
D2
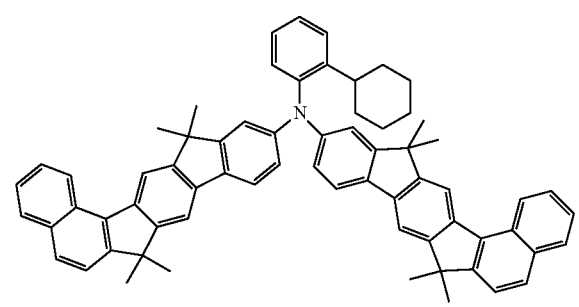 [SMILES: CC1(C)c2cc(N(c3ccc4c(c3)C(C)(C)c3cc5c(cc3-4)C(C)(C)c3ccc4ccccc4c3-5)c3ccccc3C3CCCCC3)ccc2-c2cc3c(cc21)-c1c(ccc2ccccc12)C3(C)C]
D3
TABLE 2
Data of the OLEDs
| Example | Host 95% | Dopant 5% | EQE @ 1000 cd/m² % | LT95 @ 1000 cd/m² [h] | CIE x | CIE y |
|---|---|---|---|---|---|---|
| V1 | VH-1 | D1 | 8.0 | 90 | 0.136 | 0.145 |
| V2 | VH-1 | D2 | 7.5 | 100 | 0.134 | 0.101 |
| V3 | VH-1 | D3 | 6.6 | 10 | 0.142 | 0.086 |
| V4 | VH-2 | D1 | 7.9 | 100 | 0.135 | 0.160 |
| V5 | VH-2 | D3 | 6.9 | 30 | 0.144 | 0.082 |
| E6 | H-1 | D1 | 8.3 | 150 | 0.134 | 0.147 |
| E7 | H-1 | D2 | 8.6 | 170 | 0.145 | 0.099 |
| E8 | H-1 | D3 | 7.0 | 110 | 0.144 | 0.084 |
| E9 | H-2 | D1 | 8.2 | 140 | 0.137 | 0.141 |
| E10 | H-2 | D2 | 8.5 | 150 | 0.145 | 0.093 |
| E11 | H-2 | D3 | 6.8 | 90 | 0.148 | 0.076 |
Examples E6 to E11 show in a comparative examination with Comparative Examples V1 to V5 that compounds H-1 and H-2 according to the invention achieve an improved external quantum efficiency (EQE) and an increased lifetime (LT95) with comparable deep-blue emission compared with comparative materials VH-1 and VH-2.

B-2) Device Examples Processed from Solution: Production of OLEDs

The production of solution-based OLEDs is described in principle in the literature, for example in WO 2004/037887 and WO 2010/097155. In the following examples, the two production methods (application from gas phase and solution processing) were combined, so that processing up to and including the emission layer was carried out from solution and the subsequent layers (hole-blocking layer/electron-transport layer) were applied by vacuum vapour deposition. The general processes described above are for this purpose adapted to the circumstances described here (layer-thickness variation, materials) and combined as follows.

The structure B used is thus as follows:
substrate,
ITO (50 nm),
PEDOT (20 nm),
hole-transport layer (HIL2) (20 nm),
emission layer (92% of host, 8% of dopant) (60 nm),
electron-transport layer (ETL 50%+EIL 50%) (20 nm),
cathode (Al).

The substrates used are glass plates coated with structured ITO (indium tin oxide) in a thickness of 50 nm. For better processing, these are coated with the buffer (PEDOT) Clevios P VP AI 4083 (Heraeus Clevios GmbH, Leverkusen). The spin coating is carried out from water in air. The layer is subsequently dried by heating at 180° C. for 10 minutes.

The hole-transport and emission layers are applied to the glass plates coated in this way. The hole-transport layer is the polymer of the structure shown in Table 3, which was synthesised in accordance with WO 2010/097155. The polymer is dissolved in toluene, so that the solution typically has a solids content of approx. 5 g/l if, as here, the layer thickness of 20 nm which is typical for a device is to be achieved by means of spin coating. The layers are applied by spin coating in an inert-gas atmosphere, in the present case argon, and dried by heating at 180° C. for 60 min.

The emission layer is always composed of at least one matrix material (host material) and an emitting dopant (emitter). An expression such as H-1 (92%):D1 (8%) here means that material H-1 is present in the emission layer in a proportion by weight of 92% and dopant D1 is present in the emission layer in a proportion by weight of 8%. The mixture for the emission layer is dissolved in toluene. The typical solids content of such solutions is approx. 18 g/l if, as here, the layer thickness of 60 nm which is typical for a device is to be achieved by means of spin coating. The layers are applied by spin coating in an inert-gas atmosphere, in the present case argon, and dried by heating at 140° C. for 10 minutes. The materials used are shown in Table 3.

The materials for the electron-transport layer and for the cathode are applied by thermal vapour deposition in a vacuum chamber. The electron-transport layer, for example, may consist of more than one material, which are admixed with one another in a certain proportion by volume by co-evaporation. An expression such as ETM:EIL (50%: 50%) here means that materials ETM and EIL are present in the layer in a proportion by volume of 50% each. The materials used in the present case are shown in Table 1.

TABLE 3

Structures of the materials used

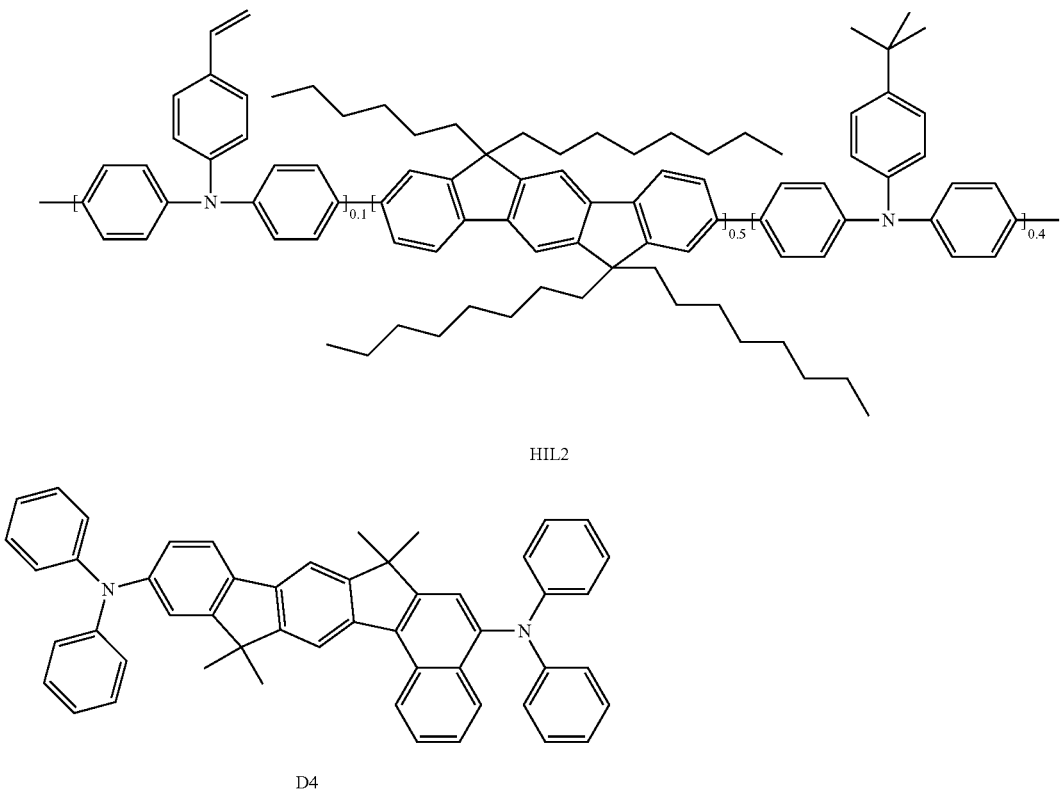

HIL2

D4

TABLE 3-continued

Structures of the materials used

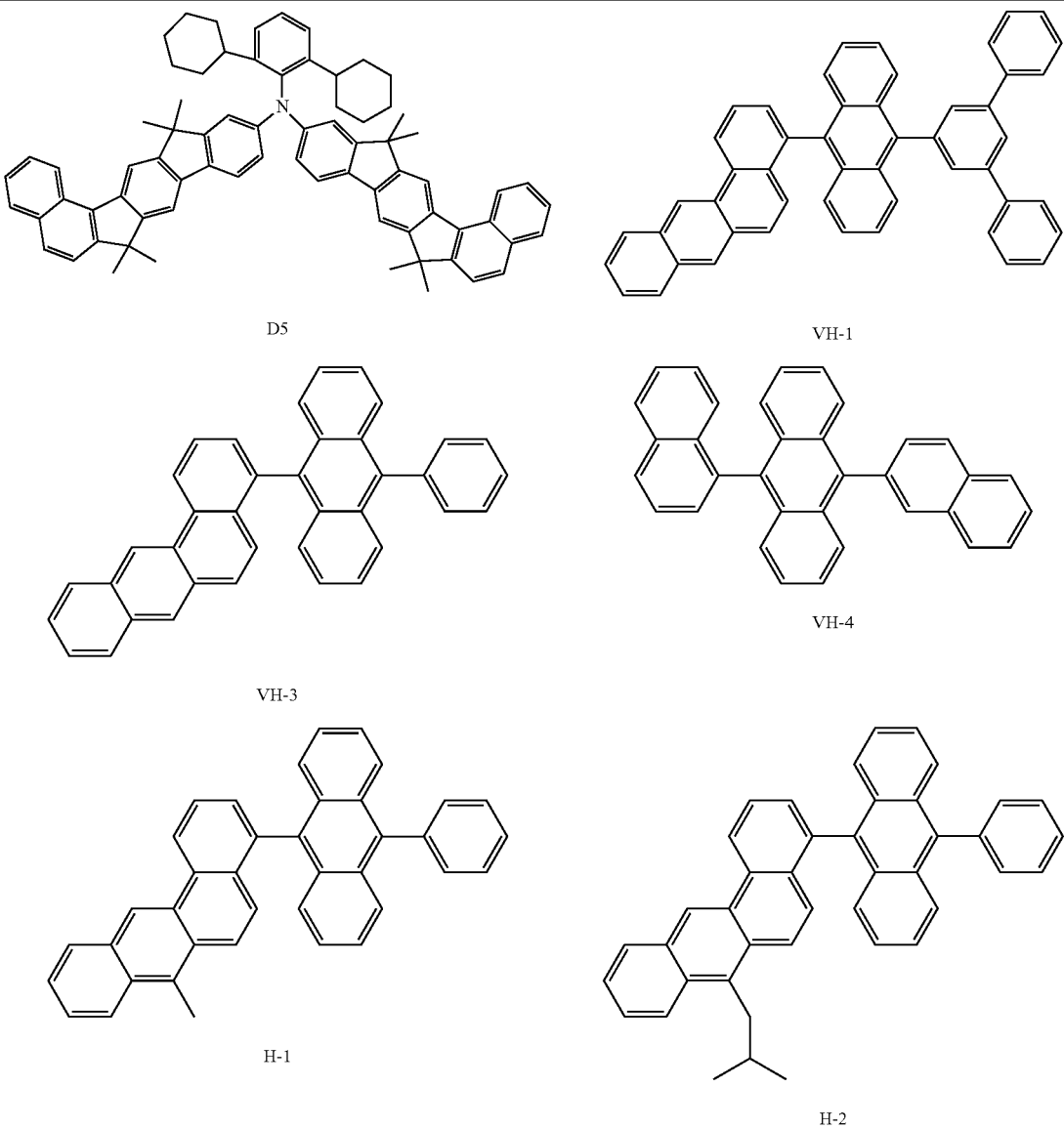

TABLE 4

Data of the OLEDs

| Example | Host 92% | Dopant 8% | EQE @ 1000 cd/m² % | LT80 @ 10 mA/ cm² [h] | CIE x | CIE y | Solubility g/l | Tg °C. |
|---|---|---|---|---|---|---|---|---|
| V6 | VH-1 | D4 | 4.8 | 200 | 0.142 | 0.211 | 70 | 175 |
| V7 | VH-1 | D5 | 3.2 | 40 | 0.142 | 0.111 | 70 | 175 |
| V8 | VH-3 | D4/D5 | X | X | X | X | <1 | 148 |
| V9 | VH-4 | D4 | 4.8 | 210 | 0.136 | 0.195 | 44 | 125 |
| V10 | VH-4 | D5 | 3.4 | 50 | 0.145 | 0.119 | 44 | 125 |
| E11 | H-1 | D4 | 5.0 | 280 | 0.137 | 0.201 | 40 | 152 |
| E12 | H-1 | D5 | 3.6 | 80 | 0.147 | 0.125 | 40 | 152 |
| E13 | H-2 | D4 | 4.8 | 300 | 0.135 | 0.197 | 45 | 143 |
| E14 | H-2 | D5 | 3.5 | 90 | 0.146 | 0.120 | 45 | 143 |

The examples of Table 4 show compounds H-1 and H-2 according to the invention as host compounds for dopants D4 and D5. As comparison, the compounds in accordance with the prior art VH-1, VH-3 and VH-4 are shown, likewise in combination with dopants D4 and D5.

The results in Table 4 show that, besides an improved external quantum efficiency, it is possible to achieve a significantly improved lifetime (LT80) with deep-blue emission both compared with VH-1 and also with VH-4.

Reference material VH-3 cannot be processed from solution at all owing to the low solubility (Example V8; X=not determined).

The structures found are thus also suitable for solution processing besides the vapour-deposition process and result in excellent performance data.

The invention claimed is:

1. A compound of formula (I-1-1):

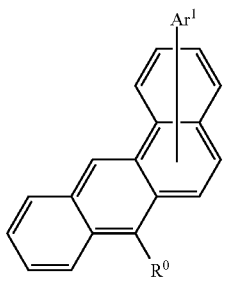

(I-1-1)

wherein
Ar¹ is an anthracene, which is optionally substituted by one or more radicals R², wherein the group Ar¹ is present at a position on the benzanthracene in formula (I-1-1) selected from the group consisting of positions 4 and 5, as depicted below:

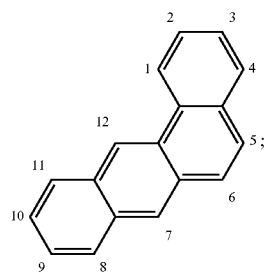 [SMILES: c1ccc2cc3c(ccc4ccccc43)cc2c1]

R⁰ is a straight-chain alkyl group having 1 to 20 C atoms or a branched alkyl group having 3 to 20 C atoms, wherein said groups are each optionally substituted by one or more radicals R³;

R² is on each occurrence, identically or differently, H, D, F, a straight-chain alkyl or alkoxy group having 1 to 20 C atoms, a branched or cyclic alkyl or alkoxy group having 3 to 20 C atoms, wherein said groups are optionally substituted by one or more radicals R³ an aromatic ring system having 6 to 40 aromatic ring atoms, which is optionally substituted by one or more radicals R³, or a heteroaromatic ring system having 5 to 40 aromatic ring atoms, which is optionally substituted by one or more radicals R³; and R³ is on each occurrence, identically or differently, H, D or F.

2. The compound of claim 1, wherein R⁰ is selected from the group consisting of straight-chain alkyl groups having 1 to 10 C atoms or branched alkyl groups having 3 to 10 C atoms, wherein said groups are each optionally substituted by one or more radicals R³.

3. A process for preparing a compound of claim 1, comprising:

A) steps 1) through 3) in the following sequence:
1) preparing a benzanthracene compound substituted by one or more aromatic or heteroaromatic ring systems via a coupling reaction between a benzanthracene derivative and an aromatic or heteroaromatic ring system;
2) halogenating the benzanthracene;
3) introducing a substituent into the halogenated position; or comprising B) steps I) and II) in the following sequence:
I) preparing a substituted benzanthracene derivative from a naphthyl derivative and a phthalic anhydride;
II) coupling the substituted benzanthracene derivative with an aromatic or heteroaromatic ring system.

4. The process of claim 3, wherein the halogenation is bromination.

5. An oligomer, polymer, or dendrimer comprising one or more compounds of claim 1, wherein the bond(s) to the polymer, oligomer, or dendrimer are optionally localised at any positions in formula (I-1-1) substituted by R⁰, R² or R³.

6. A formulation comprising at least one compound of claim 1, and at least one solvent.

7. A formulation comprising at least one oligomer, polymer, or dendrimer of claim 5 and at least one solvent.

8. An electronic device comprising at least one compound of claim 1.

9. The electronic device of claim 8, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices.

10. An electronic device comprising the least one oligomer, polymer, or dendrimer of claim 5.

11. The electronic device of claim 10, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices.

12. The electronic device of claim 9, wherein the electronic device is an organic electroluminescent device comprising an anode, a cathode, an emitting layer, and optionally further organic layers, wherein the at least one compound is present in the emitting layer as a matrix compound in combination with one or more emitter compounds.

13. The electronic device of claim 11, wherein the electronic device is an organic electroluminescent device comprising an anode, a cathode, an emitting layer, and optionally further organic layers, wherein the at least one oligomer, polymer, or dendrimer is present in the emitting layer as a matrix compound in combination with one or more emitter compounds.

* * * * *